US011246538B2

(12) United States Patent
Mitchell et al.

(10) Patent No.: US 11,246,538 B2
(45) Date of Patent: Feb. 15, 2022

(54) SINGLE CHANNEL AND DUAL CHANNEL NOISE DETECTION SYSTEMS AND TECHNIQUES

(71) Applicant: ZOLL Medical Corporation, Chelmsford, MA (US)

(72) Inventors: Jeffery T. Mitchell, Mars, PA (US); Michael A. Sipe, Pittsburgh, PA (US); Francesco Nicolo, Oakmont, PA (US)

(73) Assignee: ZOLL Medical Corporation, Chelmsford, MA (US)

(*) Notice: Subject to any disclaimer, the term of this patent is extended or adjusted under 35 U.S.C. 154(b) by 139 days.

(21) Appl. No.: 16/359,200

(22) Filed: Mar. 20, 2019

(65) Prior Publication Data

US 2020/0297233 A1    Sep. 24, 2020

(51) Int. Cl.
| | | |
|---|---|---|
| *A61B 5/04* | (2006.01) | |
| *A61B 5/0456* | (2006.01) | |
| *A61B 5/00* | (2006.01) | |
| *A61B 5/046* | (2006.01) | |
| *G16H 10/60* | (2018.01) | |

(Continued)

(52) U.S. Cl.
CPC .......... *A61B 5/7203* (2013.01); *A61B 5/0006* (2013.01); *A61B 5/316* (2021.01); *A61B 5/361* (2021.01); *A61B 5/7264* (2013.01); *A61B 5/352* (2021.01); *A61B 5/363* (2021.01); *A61B 5/366* (2021.01); *A61B 5/6833* (2013.01);

(Continued)

(58) Field of Classification Search
CPC ... A61B 5/04017; A61B 5/046; A61B 5/0464; A61B 5/0472; A61B 5/7203; A61B 5/7264; A61B 5/0006; A61B 5/316; A61B 5/361; G16H 10/60; G16H 40/60; G16H 50/30

See application file for complete search history.

(56) References Cited

U.S. PATENT DOCUMENTS

| | | |
|---|---|---|
| 5,792,062 A | 8/1998 | Poon et al. |
| 6,169,919 B1 * | 1/2001 | Nearing ............... A61B 5/0452 600/518 |

(Continued)

FOREIGN PATENT DOCUMENTS

CN    103961089    11/2015

OTHER PUBLICATIONS

K.M. Talha et al., "Removal of ECG Baseline Wander Using Savitzky-Golay Filter Based Method", Bangladesh Journal of Medical Physics, 2015, pp. 32-45, vol. 8.

(Continued)

*Primary Examiner* — Michael W Kahelin
*Assistant Examiner* — Pamela M. Bays
(74) *Attorney, Agent, or Firm* — Finch & Maloney PLLC

(57) ABSTRACT

An ECG processing system for identifying noisy ECG data segments is provided. The ECG processing system includes a network interface and a processor. The network interface is configured to receive a first collection of ECG data segments from wearable medical devices associated with a plurality of patients, each wearable medical device of the wearable medical devices being configured to be continuously worn by a patient for an extended period of time. The processor is configured to produce a second collection of ECG data segments from the first collection of ECG data segments that excludes noisy ECG data segments.

20 Claims, 17 Drawing Sheets

(51) Int. Cl.
    *A61B 5/316*     (2021.01)
    *A61B 5/361*     (2021.01)
    *G16H 50/30*     (2018.01)
    *A61B 5/352*     (2021.01)
    *A61B 5/363*     (2021.01)
    *A61B 5/366*     (2021.01)
    *G16H 40/60*     (2018.01)

(52) U.S. Cl.
    CPC ............ *G16H 10/60* (2018.01); *G16H 40/60* (2018.01); *G16H 50/30* (2018.01)

(56) References Cited

U.S. PATENT DOCUMENTS

| | | | |
|---|---|---|---|
| 2007/0027396 A1* | 2/2007 | Assaleh | A61B 5/0444 600/511 |
| 2013/0261479 A1 | 10/2013 | Kemppainen et al. | |
| 2014/0128758 A1 | 5/2014 | Galloway et al. | |
| 2015/0018702 A1 | 1/2015 | Galloway et al. | |
| 2016/0262645 A1 | 9/2016 | Herleikson | |
| 2018/0140203 A1* | 5/2018 | Wang | A61B 5/04017 |
| 2018/0168473 A1* | 6/2018 | Du | A61B 5/04085 |

OTHER PUBLICATIONS

Jiapu Pan et al., "A Real-Time QRS Detection Algorithm", IEEE Transactions on Biomedical Engineering, Mar. 1985, pp. 230-236, vol. BME-32, No. 3.

* cited by examiner

SINGLE CHANNEL AND DUAL CHANNEL NOISE DETECTION SYSTEMS AND TECHNIQUES

BACKGROUND

The present disclosure is directed to processing and determining reliability of physiological information collected by an ambulatory medical device.

A wide variety of electronic and mechanical devices can be prescribed for monitoring and treating patients' medical conditions, such as cardiac arrhythmias. One of the deadliest cardiac arrhythmias is ventricular fibrillation (VF), which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as VF, ventricular tachycardia (VT), pulseless electrical activity (PEA), and asystole result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. VF or VT can be treated by an external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

A patient at high risk of a cardiac arrhythmia may be prescribed an ambulatory monitoring and treatment device such as the ZOLL LifeVest® wearable cardioverter defibrillator available from ZOLL Medical Corporation. The device includes one or more microprocessors that operate on physiological data to assess the patient's health in accordance with predetermined criteria. For example, such physiological data can include electrocardiogram (ECG) data derived from multiple sensing electrodes in contact with the patient's skin.

SUMMARY

In at least one example, an ECG processing system for identifying noisy ECG data segments is provided. The ECG processing system includes one or more network interfaces, a memory, and one or more processors and associated circuitry. The one or more network interfaces are configured to receive a first collection of ECG data segments from wearable medical devices associated with a plurality of patients, each wearable medical device of the wearable medical devices being configured to be continuously worn by a patient for an extended period of time. The memory is configured to store the first collection of ECG data segments. The one or more processors and associated circuitry can be configured to (a) retrieve the first collection of ECG data segments from the memory and (b) for each ECG data segment in the first collection of data segment, transform each ECG data segment of the first collection of ECG data segments into a corresponding baseline representation of the ECG data segment by dividing the ECG data segment into a plurality of sample periods, each sample period of the plurality of sample periods spanning between 2 and 8 seconds; for each sample period within the plurality of sample periods, removing ECG data collected within the sample period that transgresses one or more threshold values to generate the baseline representation of the ECG data segment; fit the baseline representation of the ECG data segment to a function including at least one coefficient; compare the at least one coefficient of the function to at least one threshold value; and identify the ECG data segment as a noisy ECG data segment where the coefficient of the function transgresses the at least one threshold value. The one or more processors and associated circuitry can be further configured to (c) produce a second collection of ECG data segments from the first collection of ECG data segments that excludes the noisy ECG data segments and (d) output one or more ECG metrics relating to the plurality of patients based on the second collection of ECG data segments.

Implementations of an ECG processing system may include one or more of the following features.

In the ECG processing system, the first collection of ECG data segments can be updated over time to include additional ECG data segments. In some examples of the ECG processing system, the one or more processors is configured to periodically repeat steps (a)-(d) after a duration of time. In some examples of the ECG processing system, the duration of time can include at least one of 30 minutes, 1 hour, 4 hours, 24 hours, 1 week, 2 weeks, and 1 month. In some examples of the ECG processing system, the one or more processors can be configured to determine or more trends in the one or more ECG metrics over the duration of time.

In the ECG processing system, the function can include a polynomial. In some examples of the ECG processing system, the polynomial can include a third-degree polynomial. In some examples of the ECG processing system, the coefficient can include a coefficient of a first-degree monomial of the third-degree polynomial. In some examples of the ECG processing system, the at least one threshold value can include a range of threshold values between −0.5 and 0.5.

In the ECG processing system, the one or more processors can be further configured to analyze the first collection of ECG data segments to determine the at least one threshold value.

In the ECG processing system, the one or more processors can be configured to use linear regression to fit the baseline representation of the ECG data segment to the function.

In the ECG processing system, the one or more processors can be configured to determine, for each sample period within the plurality of sample periods, a mean of ECG data collected within the sample period; determine, for each sample period within the plurality of sample periods, a standard deviation of ECG data collected within the sample period; and determine, for each sample period within the plurality of sample periods, the one or more threshold values based on the mean of the ECG data collected within the sample period and the standard deviation of the ECG data collected within the sample period.

In the ECG processing system, each of the ECG data segments can span between 15 and 120 seconds.

In the ECG processing system, of the ECG data segments can include an average length of at least one of about 15 seconds, about 30 seconds, about 45 seconds, about 60 seconds, about 90 seconds, about 120 seconds, about 150 seconds, about 180 seconds, about 5 minutes, about 10 minutes, and about 15 minutes.

In the ECG processing system, the one or more metrics can include a heart rate metric, a heart rate variability metric, a QRS duration metric, a QT interval metric, a heart rate turbulence metric, and/or a pre-ventricular contraction (PVC) burden metric. In some examples of the ECG processing system, to output information regarding one or more ECG metrics can include to provide the one or more metrics to a cardiac prediction process.

In the ECG processing system, the one or more ECG metrics can be used to determine or one or more arrhythmia events. In some examples of the ECG processing system, the one or more arrhythmia events can include one or more of ventricular tachycardia, ventricular fibrillation, bradycardia, tachycardia, asystole, pause, bigeminy, and trigeminy.

In the ECG processing system, the system can further include the wearable medical devices, each wearable medical device including a network interface configured to communicate with the one or more network interfaces via a network; an electrocardiogram (ECG) sensor configured to couple externally to a skin of a patient of the plurality of patients and acquire ECG signals indicative of cardiac activity of the patient; and at least one processor coupled to the ECG sensor and the network interface, the at least one processor being configured to receive the ECG signals indicative of the cardiac activity of the patient, process the ECG signals to generate ECG data indicative of the cardiac activity of the patient, divide the ECG data to generate one or more ECG data segments, and transmit the one or more ECG data segments to the one or more network interfaces via the network interface, wherein the one or more processors are further configured to receive the one or more ECG data segments via the one or more network interfaces and store the one or more ECG data segments within the first collection of ECG data segments in the memory.

In some examples of the ECG processing system, at least one medical device of the wearable medical devices can further include a treatment electrode configured to couple externally to the skin of the patient of the plurality of patients and the at least one processor can be further configured to monitor the patient for an arrhythmia condition and treat the patient upon detection of the arrhythmia condition.

In the ECG processing system, each element of the ECG data can include a first field allocated to store an amplitude value and a second field allocated to store a timestamp value.

In the ECG processing system, the wearable medical devices can include dry ECG electrodes to acquire the ECG signals.

In the ECG processing system, the wearable medical devices can include adhesively attached ECG electrodes to acquire the ECG signals.

In the ECG processing system, the wearable medical devices can include a first wearable medical device associated with a first heart failure patient and a second wearable medical device associated with a second heart failure patient. In some examples of the ECG processing system, the first wearable medical device can include a first ECG sensor and the second wearable medical device can include a second ECG sensor, the ECG sensor including an adhesively attached ECG electrode to acquire the ECG signals and the second ECG sensor including a dry ECG electrode to acquire the ECG signals. In some examples of the ECG processing system, the adhesively attached electrode can be integrated with a therapy electrode within a single patch.

In the ECG processing system, the one or more ECG metrics can be analyzed to determine a current heart failure condition of at least one of the plurality of patients.

In the ECG processing system, the one or more ECG metrics can be analyzed to determine a change in the heart failure condition of the at least one of the plurality of patients.

In at least one example, an ECG processing system is provided. The ECG processing system includes one or more network interfaces, a memory, and one or more processors and associated circuitry coupled with the memory and the one or more network interfaces. The one or more network interfaces are configured to receive a first collection of ECG data segments from wearable medical devices associated with a plurality of patients, each ECG data segment including first ECG data acquired via a first channel and second ECG data acquired via a second channel, each wearable medical device of the wearable medical devices being configured to be continuously worn by a patient for an extended period of time. The memory is configured to store the first collection of ECG data segments. The and one or more processors and associated circuitry are configured to (a) retrieve the first collection of ECG data segments from the memory, (b) for each ECG data segment of the first collection of ECG data segments, (i) transform the ECG data segment into a corresponding QRS representation of the ECG data segment by identifying a first plurality of QRS complexes within the first ECG data, identifying a second plurality of QRS complexes within the second ECG data, and storing representations of the first plurality of QRS complexes and the second plurality of QRS complexes within the QRS representation of the ECG data segment, (ii) determine whether each QRS complex of the first plurality of QRS complexes matches a respective QRS complex of the second plurality of QRS complexes, (iii) determine a first average interval between QRS complexes of the first plurality of QRS complexes, (vi) determine a second average interval between QRS complexes of the second plurality of QRS complexes, (v) determine whether the first average interval differs from the second average interval by a threshold value, and (vi) identify the ECG data segment as a noisy ECG data segment where two or more consecutive QRS complexes of the first plurality of QRS complexes do not match respective QRS complexes of the second plurality of QRS complexes, and/or the first average interval differs from the second average interval by the threshold value, (c) produce a second collection of ECG data segments from the first collection of ECG data segments that excludes the noisy ECG data segments, and (d) output one or more ECG metrics relating to the plurality of patients based on the second collection of ECG data segments.

Implementations of an ECG processing system may include one or more of the following features.

In the ECG processing system, the representations stored within the QRS representation of the ECG data segment can include timestamps. In some examples of the ECG processing system, the timestamps can correspond to R waves within QRS complexes. In some examples of the ECG processing system, the first average interval and the second average interval are RR intervals.

In the ECG processing system, to determine whether each QRS complex of the first plurality of QRS complexes matches a respective QRS complex of the second plurality of QRS complexes can include to compare a first timestamp of each QRS complex of the first plurality of QRS complexes to a second timestamp of the respective QRS complex of the second plurality of QRS complexes; determine a match where the first timestamp and the second timestamp are within a range; and determine no match where the first timestamp and the second timestamp are outside the range. In some examples of the ECG processing system, the range can be between 50 and 500 milliseconds.

In the ECG processing system, the threshold value can be between 10% and 40%.

In the ECG processing system, the one or more processors can be further configured to, for each QRS complex of the first plurality of QRS complexes and the second plurality of QRS complexes, determine an amplitude of an R wave within the QRS complex, determine a high frequency signal-to-noise ratio of the QRS complex, compare the amplitude to at least one first threshold value, compare the high frequency signal-to-noise ratio to at least one second threshold value, and record the QRS complex as a noisy QRS complex where the amplitude transgresses the at least one first threshold value, and/or the high frequency signal-to-noise ratio of the QRS complex is below the at least one second threshold value.

In the ECG processing system, the one or more processors can be further configured to, for each QRS complex of the first plurality of QRS complexes and the second plurality of QRS complexes, determine a first isoelectric level estimate for a first QRS complex, determine a second isoelectric level estimate for a QRS complex adjacent to the first QRS complex, determine a difference between the first isoelectric level estimate and the second isoelectric level estimate, and record the QRS complex as a noisy QRS complex where the difference between the first isoelectric level estimate and the second isoelectric level estimate transgresses a threshold value.

In the ECG processing system, the one or more ECG metrics can be used to determine or one or more arrhythmia events. In some examples of the ECG processing system, the one or more arrhythmia events can include one or more of ventricular tachycardia, ventricular fibrillation, bradycardia, tachycardia, asystole, pause, bigeminy, and trigeminy.

In at least one example, an ECG processing system is provided. The ECG processing system includes one or more network interfaces, a memory, and one or more processors coupled with the one or more network interfaces and the memory. The one or more network interfaces are configured to receive a collection of ECG data segments from a plurality of wearable medical devices associated with a plurality of patients, each wearable medical device of the wearable medical devices being configured to be continuously worn by a patient for an extended period of time. The memory is configured to store the collection of ECG data segments. The one or more processors are configured to retrieve the collection of ECG data segments from the memory, for each ECG data segment of the collection of ECG data segments, transform the ECG data segment into a corresponding QRS representation of the ECG data segment by identifying a plurality of QRS complexes within the ECG data segment, and store representations of the plurality of QRS complexes within the QRS representation of the ECG data segment, establish a sliding window into the plurality of QRS complexes, the sliding window iteratively identifying sets of QRS complexes within the plurality of QRS complexes, for each set of QRS complexes identified via the sliding window, determine intervals between consecutive QRS complexes of the set of QRS complexes, identify a candidate QRS complex from the set of QRS complexes as being a potential pre-ventricular contraction (PVC) using the intervals, determine whether the candidate QRS complex matches a template, determine whether the candidate QRS complex matches other QRS complexes of the set of QRS complexes where the candidate QRS complex does not match the template, and record the candidate QRS complex as a PVC where the candidate QRS complex does not match another QRS complex of the set of QRS complexes, and output one or more ECG metrics relating to the plurality of patients based on ECG data segments of the collection other than ECG data segments including a QRS complexes recorded as a PVC.

Implementations of an ECG processing system may include one or more of the following features.

In the ECG processing system, each set of QRS complexes can include 6 QRS complexes from the plurality of QRS complexes, the sliding window can initially identify a first 6 QRS complexes from the plurality of QRS complexes, and the sliding window can iterate by 1 QRS complex at a time.

In the ECG processing system, the intervals can include 5 RR intervals. In some examples of the ECG processing system, to identify the candidate QRS complex includes to identify a compensatory pause in the intervals. In some examples ECG processing system, the one or more processors are further configured to analyze ECG data to determine the template.

In at least one example, a method of identifying noisy ECG data segments is provided. The method includes receiving, by one or more network interfaces, a first collection of ECG data segments from wearable medical devices associated with a plurality of patients, each wearable medical device of the wearable medical devices being configured to be continuously worn by a patient for an extended period of time; storing, by a memory, the first collection of ECG data segments; and retrieving, by one or more processors operably coupled to the memory, the first collection of ECG data segments from the memory. For each ECG data segment of the first collection of ECG data segments, the method includes transforming, by the one or more processors, the ECG data segment into a corresponding baseline representation of the ECG data segment by dividing the ECG data segment into a plurality of sample periods, each sample period of the plurality of sample periods spanning between 2 and 8 seconds, and for each sample period within the plurality of sample periods, removing, by the one or processors, ECG data collected within the sample period that transgresses one or more threshold values to generate the baseline representation of the ECG data segment, fitting, by the one or more processors, the baseline representation of the ECG data segment to a function including at least one coefficient, comparing, by the one or more processors, the at least one coefficient of the function to at least one threshold value, and identifying, by the one or more processors, the ECG data segment as a noisy ECG data segment where the coefficient of the function transgresses the at least one threshold value. The method further includes producing, by the one or more processors, a second collection of ECG data segments from the first collection of ECG data segments that excludes the noisy ECG data segments and outputting, by the one or more processors, one or more ECG metrics relating to the plurality of patients based on the second collection of ECG data segments.

Implementations of the method may include one or more of the following features.

In some examples, the method can include updating the first collection of ECG data segments over time to include additional ECG data segments. In some examples, the method can further include periodically repeating, after a duration of time, retrieving the first collection of ECG data segments from the memory, processing each ECG data segment of the first collection of ECG data segments to identify noisy ECG segments as described above, producing the second collection of ECG data segments from the first collection that excludes the noisy ECG data segments, and outputting one or more ECG metrics relating to the plurality of patients based on the second collection of ECG data segment. In some additional examples, the duration of time can include at least one of 30 minutes, 1 hour, 4 hours, 24 hours, 1 week, 2 weeks, and 1 month. In some additional examples, the method can further include determining, by the one or more processors, one or more trends in the one or more ECG metrics over the duration of time.

In the method, fitting the baseline representation of the ECG data segment to a function can include fitting the baseline representation of the ECG data segment to a polynomial. In some examples of the method, fitting the baseline representation of the ECG data segment to a polynomial can include fitting the baseline representation of the ECG data segment to a third-degree polynomial. In some examples of the method, comparing the at least one coefficient of the function to at least one threshold value can include comparing a coefficient of a first-degree monomial of the third-degree polynomial to at least one threshold value. In some examples of the method, comparing the coefficient of the first-degree monomial of the third-degree polynomial to at least one threshold value can include comparing the coefficient of the first-degree monomial of the third-degree polynomial to a range of threshold values between −0.5 and 0.5.

In some examples, the method can include analyzing, by the one or more processors, the first collection of ECG data segments to determine the at least one threshold value.

In some examples, the method can include using, by the one or more processors, linear regression to fit the baseline representation of the ECG data segment to the function.

In some examples, the method can include determining, by the one or more processors for each sample period within the plurality of sample periods, a mean of ECG data collected within the sample period; determining, by the one or more processors for each sample period within the plurality of sample periods, a standard deviation of ECG data collected within the sample period; and determining, by the one or more processors for each sample period within the plurality of sample periods, the one or more threshold values based on the mean of the ECG data collected within the sample period and the standard deviation of the ECG data collected within the sample period.

In the method, receiving the first collection of ECG data segments can include receiving ECG data segments that each span between 15 and 120 seconds.

In the method, receiving the first collection of ECG data segments can include receiving a first collection of ECG data segments having an average length of at least one of about 15 seconds, about 30 seconds, about 45 seconds, about 60 seconds, about 90 seconds, about 120 seconds, about 150 seconds, about 180 seconds, about 5 minutes, about 10 minutes, and about 15 minutes.

In the method, outputting the one or more ECG metrics can include outputting a heart rate metric, a heart rate variability metric, a QRS duration metric, a QT interval metric, a heart rate turbulence metric, and/or PVC burden metric. In some examples of the method, outputting information regarding one or more ECG metrics can include providing, by the one or more processors, the one or more ECG metrics to a cardiac prediction process.

In some examples, the method can include determining, by the one or more processors, one or more arrhythmia events based upon the one or more ECG metrics. In some examples of the method, determining the one or more arrhythmia events can include determining one or more of ventricular tachycardia, ventricular fibrillation, bradycardia, tachycardia, asystole, pause, bigeminy, and trigeminy.

In the method, receiving the first collection of ECG data segments from the wearable medical devices can include receiving a first collection of ECG data segments from wearable medical devices that each include a network interface configured to communicate with the one or more network interfaces via a network; an ECG sensor configured to couple externally to a skin of a patient of the plurality of patients and acquire ECG signals indicative of cardiac activity of the patient; and at least one processor coupled to the ECG sensor and the network interface, the at least one processor being configured to receive the ECG signals indicative of the cardiac activity of the patient, process the ECG signals to generate ECG data indicative of the cardiac activity of the patient, divide the ECG data to generate one or more ECG data segments, and transmit the one or more ECG data segments to the one or more network interfaces via the network interface, and wherein the one or more processors can be configured to receive the one or more ECG data segments via the one or more network interfaces, and store the one or more ECG data segments within the first collection of ECG data segments in the memory. In some examples of the method, at least one medical device of the wearable medical devices further can include a treatment electrode configured to couple externally to the skin of the patient of the plurality of patients and the at least one processor can be further configured to monitor the patient for an arrhythmia condition and treat the patient upon detection of the arrhythmia condition.

In the method, receiving the first collection of ECG data segments can include receiving ECG data segments in which each element of the ECG data includes a first field allocated to store an amplitude value and a second field allocated to store a timestamp value.

In some examples of the method, receiving the first collection of ECG data segments from the wearable medical devices can include receiving the first collection of ECG data segments from wearable medical devices including dry ECG electrodes to acquire the ECG signals. In some examples of the method, receiving the first collection of ECG data segments from the wearable medical devices can include receiving the first collection of ECG data segments from wearable medical devices including adhesively attached ECG electrodes to acquire the ECG signals. In some examples of the method, receiving the first collection of ECG data segments from the wearable medical devices can include receiving ECG data segments from a first wearable medical device associated with a first heart failure patient and a second wearable medical device associated with a second heart failure patient. In some examples of the method, receiving the ECG data segments from the first wearable medical device and the second wearable medical device can include receiving ECG data segments from a first wearable medical device including a first ECG sensor and a second wearable medical device including a second ECG sensor. In some examples of the method, receiving the ECG data segments from the first wearable medical device and the second wearable medical device can include acquiring first ECG signals via the first ECG sensor and acquiring second ECG signals via the second ECG sensor. In some examples of the method, acquiring the first ECG signals via the first ECG sensor and acquiring the second ECG signals via the second ECG sensor can include acquiring the first ECG signals via an adhesively attached ECG electrode and acquiring the second ECG signals via a dry ECG electrode. In some examples of the method, acquiring the first ECG signals via the first ECG sensor can include acquiring the first ECG signals via an adhesively attached ECG electrode that is integrated with a therapy electrode within a single patch.

In some examples, the method can include analyzing, by the one or more processors, the one or more ECG metrics to determine a current heart failure condition of at least one of the plurality of patients. In some examples of the method, the one or more ECG metrics are analyzed to determine a change in the current heart failure condition of the at least one of the plurality of patients.

In at least one example, a method for identifying noisy electrocardiogram (ECG) data segments is provided. The method includes receiving, by one or more network interfaces, a first collection of ECG data segments from wearable medical devices associated with a plurality of patients, each ECG data segment including first ECG data acquired via a first channel and second ECG data acquired via a second channel, each wearable medical device of the wearable medical devices being configured to be continuously worn by a patient for an extended period of time; storing, by a memory, the first collection of ECG data segments; and retrieving, by one or more processors operably coupled to the memory, the first collection of ECG data segments from the memory. The method further includes, for each ECG data segment of the first collection of ECG data segments, transforming, by the one or more processors, the ECG data segment into a corresponding QRS representation of the ECG data segment by identifying a first plurality of QRS complexes within the first ECG data, identifying a second plurality of QRS complexes within the second ECG data, and storing representations of the first plurality of QRS complexes and the second plurality of QRS complexes within the QRS representation of the ECG data segment, determining, by the one or more processors, whether each QRS complex of the first plurality of QRS complexes matches a respective QRS complex of the second plurality of QRS complexes, determining, by the one or more processors, a first average interval between QRS complexes of the first plurality of QRS complexes, determining, by the one or more processors, a second average interval between QRS complexes of the second plurality of QRS complexes, determining, by the one or more processors, whether the first average interval differs from the second average interval by a threshold value, and identifying, by the one or more processors, the ECG data segment as a noisy ECG data segment where two or more consecutive QRS complexes of the first plurality of QRS complexes do not match respective QRS complexes of the second plurality of QRS complexes and/or the first average interval differs from the second average interval by the threshold value. The method also includes producing, by the one or more processors, a second collection of ECG data segments from the first collection of ECG data segments that excludes the noisy ECG data segments and outputting, by the one or more processors, one or more ECG metrics relating to the plurality of patients based on the second collection of ECG data segments.

Implementations of the method may include one or more of the following features.

In the method, the representations stored within the QRS representation of the ECG data segment can include timestamps. In some examples of the method, the timestamps stored in the QRS representation can correspond to R waves within QRS complexes. In some examples of the method, the first average interval and the second average interval determined by the one or more processors can be RR intervals.

In the method, determining whether each QRS complex of the first plurality of QRS complexes matches a respective QRS complex of the second plurality of QRS complexes can include comparing, by the one or more processors, a first timestamp of each QRS complex of the first plurality of QRS complexes to a second timestamp of the respective QRS complex of the second plurality of QRS complexes; determining, by the one or more processors, a match where the first timestamp and the second timestamp are within a range; and determining, by the one or more processors, no match where the first timestamp and the second timestamp are outside the range. In some examples of the method, the range can be between 50 and 500 milliseconds.

In the method, the threshold value determined by the one or more processors can be between 10% and 40%.

In some examples, the method can include, for each QRS complex of the first plurality of QRS complexes and the second plurality of QRS complexes determining, by the one or more processors, an amplitude of an R wave within the QRS complex, determining, by the one or more processors, a high frequency signal-to-noise ratio of the QRS complex, comparing, by the one or more processors, the amplitude to at least one first threshold value, comparing, by the one or more processors, the high frequency signal-to-noise ratio to at least one second threshold value, and recording, by the one or more processors, the QRS complex as a noisy QRS complex where the amplitude transgresses the at least one first threshold value and/or the high frequency signal-to-noise ratio of the QRS complex is below the at least one second threshold value.

In some examples, the method can include, for each QRS complex of the first plurality of QRS complexes and the second plurality of QRS complexes, determining, by the one or more processors, a first isoelectric level estimate for a first QRS complex, determining, by the one or more processors, a second isoelectric level estimate for a QRS complex adjacent to the first QRS complex, determining, by the one or more processors, a difference between the first isoelectric level estimate and the second isoelectric level estimate, and recording, by the one or more processors, the QRS complex as a noisy QRS complex where the difference between the first isoelectric level estimate and the second isoelectric level estimate transgresses a threshold value.

In the method, the one or more ECG metrics can be used to determine or one or more arrhythmia events. In some examples of the method, the one or more arrhythmia events determined using the one or more ECG metrics can include one or more of ventricular tachycardia, ventricular fibrillation, bradycardia, tachycardia, asystole, pause, bigeminy, and trigeminy.

In at least one example, a method is provided. The method includes receiving, by one or more network interfaces, a collection of ECG data segments from a plurality of wearable medical devices associated with a plurality of patients, each wearable medical device of the wearable medical devices being configured to be continuously worn by a patient for an extended period of time; storing, by a memory, the collection of ECG data segments; and retrieving, by one or more processors operably coupled to the memory, the collection of ECG data segments from the memory. For each ECG data segment of the collection of ECG data segments, the method also includes transforming, by the one or more processors, the ECG data segment into a corresponding QRS representation of the ECG data segment by identifying a plurality of QRS complexes within the ECG data segment and storing representations of the plurality of QRS complexes within the QRS representation of the ECG data segment, establishing, by the one or more processors, a sliding window into the plurality of QRS complexes, the sliding window iteratively identifying sets of QRS complexes within the plurality of QRS complexes. For each set of QRS complexes identified via the sliding window, the method also includes determining, by the one or more processors, intervals between consecutive QRS complexes of the set of QRS complexes, identifying, by the one or more processors, a candidate QRS complex from the set of QRS complexes as being a potential pre-ventricular contraction (PVC) using the intervals, determining, by the one or more processors, whether the candidate QRS complex matches a template, determining, by the one or more processors, whether the candidate QRS complex matches other QRS complexes of the set of QRS complexes where the candidate QRS complex does not match the template, and recording, by the one or more processors, the candidate QRS complex as a PVC where the candidate QRS complex does not match another QRS complex of the set of QRS complexes. The method further includes outputting, by the one or more processors, one or more ECG metrics relating to the plurality of patients based on ECG data segments of the collection other than ECG data segments including a QRS complexes recorded as a PVC.

Implementations of the method may include one or more of the following features.

In the method, each set of QRS complexes iteratively identified by the one or more processors via the sliding window can include 6 QRS complexes from the plurality of QRS complexes. In the method, the sliding window can initially identify a first 6 QRS complexes from the plurality of QRS complexes and the sliding window can iterate by 1 QRS complex at a time.

In the method, the intervals determined by the one or more processors can include 5 RR intervals.

In the method, identifying the candidate QRS complex can include identifying, by the one or more processors, a compensatory pause in the intervals.

In some examples, the method can further include analyzing, by the one or more processors, ECG data to determine the template.

In at least one example, a non-transitory computer-readable medium is provided. The non-transitory computer-readable medium has computer-executable instructions stored thereon that, when executed by one or more processors, cause the one or more processors to retrieve a first collection of ECG data segments from a memory operably coupled to the one or more processors, wherein the first collection of ECG data segments is received from wearable medical devices associated with a plurality of patients, each wearable medical device of the wearable medical devices being configured to be worn continuously by a patient for an extended period of time; for each ECG data segment of the first collection of ECG data segments, transform the ECG data segment into a corresponding baseline representation of the ECG data segment by dividing the ECG data segment into a plurality of sample periods, each sample period of the plurality of sample periods spanning between 2 and 8 seconds and, for each sample period within the plurality of sample periods, remove ECG data collected within the sample period that transgresses one or more threshold values to generate the baseline representation of the ECG data segment, fit the baseline representation of the ECG data segment to a function comprising at least one coefficient, compare the at least one coefficient of the function to at least one threshold value, and identify the ECG data segment as a noisy ECG data segment where the coefficient of the function transgresses the at least one threshold value; produce a second collection of ECG data segments from the first collection of ECG data segments that excludes the noisy ECG data segments; and output one or more ECG metrics relating to the plurality of patients based on the second collection of ECG data segments.

Implementations of the non-transitory computer-readable medium may include one or more of the following features.

In the non-transitory computer-readable medium, the computer-executable instructions can further include additional instructions that, when executed by the one or more processors, cause the one or more processors to update the first collection of ECG data segments over time to include additional ECG data segments. In some examples of the non-transitory computer-readable medium, the computer-executable instructions can further include additional instructions that, when executed by the one or more processors, cause the one or more processors to periodically repeat, after a duration of time, steps (a)-(d). In some examples of the non-transitory computer-readable medium, the duration of time can include at least one of 30 minutes, 1 hour, 4 hours, 24 hours, 1 week, 2 weeks, and 1 month. In some examples of the non-transitory computer-readable medium, the computer-executable instructions can further include additional instructions that, when executed by the one or more processors, cause the one or more processors to determine one or more trends in the one or more ECG metrics over the duration of time.

In the non-transitory computer-readable medium, the function can include a polynomial. In some examples of the non-transitory computer-readable medium, the polynomial can include a third-degree polynomial. In some examples of the non-transitory computer-readable medium, the coefficient can include a coefficient of a first-degree monomial of the third-degree polynomial. In some examples of the non-transitory computer-readable medium, the at least one threshold value can include a range of threshold values between −0.5 and 0.5.

In the non-transitory computer-readable medium, the computer-executable instructions can further include additional instructions that, when executed by the one or more processors, cause the one or more processors to analyze the first collection of ECG data segments to determine the at least one threshold value.

In the non-transitory computer-readable medium, the computer-executable instructions can further include additional instructions that, when executed by the one or more processors, cause the one or more processors to use linear regression to fit the baseline representation of the ECG data segment to the function.

In the non-transitory computer-readable medium, the computer-executable instructions can further include additional instructions that, when executed by the one or more processors, cause the one or more processors to: determine, for each sample period within the plurality of sample periods, a mean of ECG data collected within the sample period; determine, for each sample period within the plurality of sample periods, a standard deviation of ECG data collected within the sample period; and determine, for each sample period within the plurality of sample periods, the one or more threshold values based on the mean of the ECG data collected within the sample period and the standard deviation of the ECG data collected within the sample period.

In the non-transitory computer-readable medium, each of the ECG data segments can span between 15 and 120 seconds.

In the non-transitory computer-readable medium, each of the ECG data segments can include an average length of at least one of about 15 seconds, about 30 seconds, about 45 seconds, about 60 seconds, about 90 seconds, about 120 seconds, about 150 seconds, about 180 seconds, about 5 minutes, about 10 minutes, and about 15 minutes.

In the non-transitory computer-readable medium, the one or more ECG metrics can include a heart rate metric, a heart rate variability metric, a QRS duration metric, a QT interval metric, a heart rate turbulence metric, and/or a PVC burden metric. In some examples of the non-transitory computer-readable medium, the computer-executable instructions that cause the one or more processors to output information regarding one or more ECG metrics can include additional instructions that, when executed, cause the one or more processors to provide the one or more ECG metrics to a cardiac prediction process.

In the non-transitory computer-readable medium, the computer-executable instructions can further include additional instructions that, when executed by the one or more processors, cause the one or more processors to determine one or more arrhythmia events based upon the one or more ECG metrics. In some examples of the non-transitory computer-readable medium, the one or more arrhythmia events can include one or more of ventricular tachycardia, ventricular fibrillation, bradycardia, tachycardia, asystole, pause, bigeminy, and trigeminy.

In the non-transitory computer-readable medium, each of the wearable medical devices can include a network interface configured to communicate with the one or more network interfaces via a network; an electrocardiogram (ECG) sensor configured to couple externally to a skin of a patient of the plurality of patients and acquire ECG signals indicative of cardiac activity of the patient; and at least one processor coupled to the ECG sensor and the network interface, the at least one processor being configured to receive the ECG signals indicative of the cardiac activity of the patient, process the ECG signals to generate ECG data indicative of the cardiac activity of the patient, divide the ECG data to generate one or more ECG data segments, and transmit the one or more ECG data segments to the one or more network interfaces via the network interface; and the computer-executable instructions can further include additional instructions that, when executed by the one or more processors, cause the one or more processors to receive the one or more ECG data segments via the one or more network interfaces and store the one or more ECG data segments within the first collection of ECG data segments in the memory. In some examples of the non-transitory computer-readable medium, at least one medical device of the wearable medical devices can further include a treatment electrode configured to couple externally to the skin of the patient of the plurality of patients and the at least one processor can be further configured to monitor the patient for an arrhythmia condition and treat the patient upon detection of the arrhythmia condition.

In the non-transitory computer-readable medium, each element of the ECG data can include a first field allocated to store an amplitude value and a second field allocated to store a timestamp value.

In the non-transitory computer-readable medium, the wearable medical devices can include dry ECG electrodes to acquire the ECG signals. In some examples of the non-transitory computer-readable medium, the wearable medical devices can include adhesively attached ECG electrodes to acquire the ECG signals. In some examples of the non-transitory computer-readable medium, the wearable medical devices can include a first wearable medical device associated with a first heart failure patient and a second wearable medical device associated with a second heart failure patient. In some examples of the non-transitory computer-readable medium, the first wearable medical device can include a first ECG sensor and the second wearable medical device can include a second ECG sensor, the first ECG sensor including an adhesively attached ECG electrode to acquire the ECG signals and the second ECG sensor including a dry ECG electrode to acquire the ECG signals. In some examples of the non-transitory computer-readable medium, the adhesively attached ECG electrode can be integrated with a therapy electrode within a single patch.

In the non-transitory computer-readable medium, the computer-executable instructions can further include additional instructions that, when executed by the one or more processors, cause the one or more processors to analyze the one or more ECG metrics to determine a current heart failure condition of at least one of the plurality of patients. In some examples of the non-transitory computer-readable medium, the computer-executable instructions that, when executed by the one or more processors, cause the one or more processors to analyze the one or more ECG metrics can further include additional instructions that, when executed, cause the one or more processors to determine a change in the current heart failure condition of the at least one of the plurality of patients.

In at least one example, a non-transitory computer-readable medium is provided. The non-transitory computer-readable medium has computer-executable instructions stored thereon that, when executed by one or more processors, cause the one or more processors to retrieve a first collection of ECG data segments from a memory operably coupled to the one or more processors, wherein the first collection of ECG data segments is received from wearable medical devices associated with a plurality of patients, each wearable medical device of the wearable medical devices being configured to be worn continuously by a patient for an extended period of time; for each ECG data segment of the first collection of ECG data segments, transform the ECG data segment into a corresponding QRS representation of the ECG data segment by identifying a first plurality of QRS complexes within the first ECG data, identifying a second plurality of QRS complexes within the second ECG data, and storing representations of the first plurality of QRS complexes and the second plurality of QRS complexes within the QRS representation of the ECG data segment, determine whether each QRS complex of the first plurality of QRS complexes matches a respective QRS complex of the second plurality of QRS complexes, determine a first average interval between QRS complexes of the first plurality of QRS complexes, determine a second average interval between QRS complexes of the second plurality of QRS complexes, determine whether the first average interval differs from the second average interval by a threshold value, and identify the ECG data segment as a noisy ECG data segment where two or more consecutive QRS complexes of the first plurality of QRS complexes do not match respective QRS complexes of the second plurality of QRS complexes and/or the first average interval differs from the second average interval by the threshold value; produce a second collection of ECG data segments from the first collection of ECG data segments that excludes the noisy ECG data segments; and output one or more ECG metrics relating to the plurality of patients based on the second collection of ECG data segments.

Implementations of the non-transitory computer-readable medium may include one or more of the following features.

In the non-transitory computer-readable medium, the representations stored within the QRS representation of the ECG data segment can include timestamps. In some examples of the non-transitory computer-readable medium, the timestamps can correspond to R waves within QRS complexes. In some examples of the non-transitory computer-readable medium, the first average interval and the second average interval can be RR intervals.

In the non-transitory computer-readable medium, the computer-executable instructions that, when executed by the one or more processors, cause the one or more processors to determine whether each QRS complex of the first plurality of QRS complexes matches a respective QRS complex of the second plurality of QRS complexes can include additional instructions that, when executed, cause the one or more processors to compare a first timestamp of each QRS complex of the first plurality of QRS complexes to a second timestamp of the respective QRS complex of the second plurality of QRS complexes; determine a match where the first timestamp and the second timestamp are within a range; and determine no match where the first timestamp and the second timestamp are outside the range.34. The non-transitory computer-readable medium of claim 33, wherein range is between 50 and 500 milliseconds.

In the non-transitory computer-readable medium, the threshold value can be between 10% and 40%.

In the non-transitory computer-readable medium, the computer-executable instructions can further include additional instructions that, when executed by the one or more processors, cause the one or more processors to, for each QRS complex of the first plurality of QRS complexes and the second plurality of QRS complexes, determine an amplitude of an R wave within the QRS complex, determine a high frequency signal-to-noise ratio of the QRS complex, compare the amplitude to at least one first threshold value, compare the high frequency signal-to-noise ratio to at least one second threshold value, and record the QRS complex as a noisy QRS complex where the amplitude transgresses the at least one first threshold value and/or the high frequency signal-to-noise ratio of the QRS complex is below the at least one second threshold value.

In the non-transitory computer-readable medium, the computer-executable instructions can further include additional instructions that, when executed by the one or more processors, cause the one or more processors to, for each QRS complex of the first plurality of QRS complexes and the second plurality of QRS complexes, determine a first isoelectric level estimate for a first QRS complex, determine a second isoelectric level estimate for a QRS complex adjacent to the first QRS complex, determine a difference between the first isoelectric level estimate and the second isoelectric level estimate, and record the QRS complex as a noisy QRS complex where the difference between the first isoelectric level estimate and the second isoelectric level estimate transgresses a threshold value.

In the non-transitory computer-readable medium, the one or more ECG metrics can be used to determine one or more arrhythmia events. In some examples of the non-transitory computer-readable medium, the one or more arrhythmia events can include one or more of ventricular tachycardia, ventricular fibrillation, bradycardia, tachycardia, asystole, pause, bigeminy, and trigeminy.

In at least one example, a non-transitory computer-readable medium is provided. The non-transitory computer-readable medium has computer-executable instructions stored thereon that, when executed by one or more processors, cause the one or more processors to retrieve a first collection of ECG data segments from a memory operably coupled to the one or more processors, wherein the first collection of ECG data segments is received from wearable medical devices associated with a plurality of patients, each wearable medical device of the wearable medical devices being configured to be worn continuously by a patient for an extended period of time; for each ECG data segment of the collection of ECG data segments, transform the ECG data segment into a corresponding QRS representation of the ECG data segment by identifying a plurality of QRS complexes within the ECG data segment and storing representations of the plurality of QRS complexes within the QRS representation of the ECG data segment, establish a sliding window into the plurality of QRS complexes, the sliding window iteratively identifying sets of QRS complexes within the plurality of QRS complexes, for each set of QRS complexes identified via the sliding window, determine intervals between consecutive QRS complexes of the set of QRS complexes, identify a candidate QRS complex from the set of QRS complexes as being a potential pre-ventricular contraction (PVC) using the intervals, determine whether the candidate QRS complex matches a template, determine whether the candidate QRS complex matches other QRS complexes of the set of QRS complexes where the candidate QRS complex does not match the template, and record the candidate QRS complex as a PVC where the candidate QRS complex does not match another QRS complex of the set of QRS complexes; and output one or more ECG metrics relating to the plurality of patients based on ECG data segments of the collection other than ECG data segments comprising a QRS complexes recorded as a PVC.

Implementations of the non-transitory computer-readable medium may include one or more of the following features.

In the non-transitory computer-readable medium, each set of QRS complexes can include 6 QRS complexes from the plurality of QRS complexes, the sliding window can initially identify a first 6 QRS complexes from the plurality of QRS complexes, and the sliding window can iterate by 1 QRS complex at a time.

In the non-transitory computer-readable medium, the intervals can include 5 RR intervals.

In the non-transitory computer-readable medium, the computer-executable instructions that, when executed by the one or more processors, cause the one or more processors to identify the candidate QRS complex can include additional instructions that, when executed, cause the one or more processors to identify a compensatory pause in the intervals.

In the non-transitory computer-readable medium, the computer-executable instructions can further include additional instructions that, when executed by the one or more processors, cause the one or more processors to analyze ECG data to determine the template.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1A:
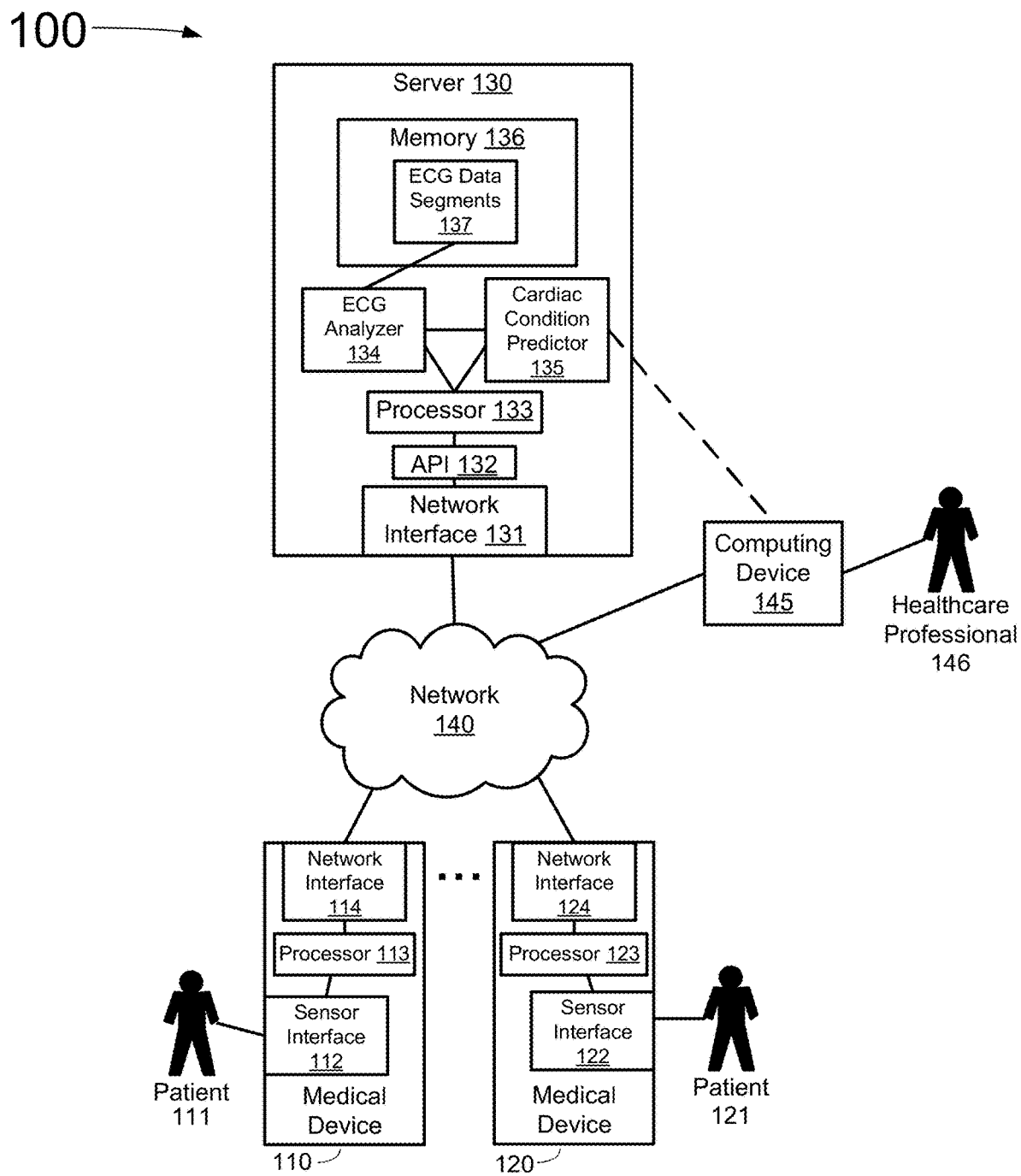
FIG. 1A depicts an overview of a computing system for processing information collected by one or more medical devices, in accordance with an example of the present disclosure.

Implementations described herein are directed to systems, devices, and methods to process electronically stored ECG signals. The processing as described herein generates a collection of groomed ECG data that that better represents patient cardiac function than ungroomed ECG signals. This collection of ECG data may include ECG data from a broad population of patients or be specific to an individual patient. In some examples, the collection of groomed ECG data includes distinct ECG data segments that each represent a patient's cardiac function as recorded over a continuous period of time. These periods of time can have durations that are range from a few seconds to several minutes. The grooming as described herein includes one or more pre-processing, transforming, adjusting, filtering, and/or converting the electronically stored ECG data to prepare such data for certain applications. For example, such applications may perform better or produce better results when the ECG data is prepared in manners described herein than when not prepared in such manners.

In this disclosure, Applicants describe systems, devices, processes, and techniques to address certain disadvantages to using ECG data sets that are not processed in the manners described herein. For example, when grooming the data sets, noisy or otherwise aberrant ECG data as determined using the techniques described herein can be removed from collections of ECG data, thereby providing for a reliable collection of groomed ECG data for later analysis in applications. Aberrations that can be detected and thus removed by certain examples disclosed herein include baseline or isoelectric line drift or wander and PVCs, among other aberrations. Similarly, by using various processes to analyze and identify noisy or otherwise aberrant ECG data as is described herein, criteria used for identifying noisy ECG data can be varied or otherwise altered, thereby providing for customizable analyzing processes used to groom the collection of ECG data. Such groomed ECG data can be more reliable than conventionally-processed ECG data, for example, because of such ability to vary or otherwise alter the criteria to customize the output ECG data sets according to the needs of the applications. Aberrant ECG data or data that diverge from such criteria may be considered noisy ECG data and addressed in the manner described herein.

Thus, in accordance with various examples disclosed herein, Applicants have developed various systems, devices, and methods to process previously acquired and stored ECG signals to generate the groomed collection of ECG data. The stored ECG signals may be single lead ECG signals, dual-lead ECG signals, or include signals from more than two leads. To produce the collection of ECG data described above, the systems and methods described herein may include one or more of the following features. In some examples, the system includes a server that executes an ECG analyzer that is configured to filter a set of stored, unfiltered ECG data segments to remove ECG data segments that include more than acceptable amount of noise. In these examples, the ECG analyzer retrieves one or more ECG data segments and analyzes the ECG data segments using either a single channel noise discrimination process or a dual channel noise discrimination process. Both of these noise discrimination process are computationally simple in that they do not require a high number of iterations, unlike other noise discrimination and remediation processes. As such, the techniques described herein can be extended as appropriate to address additional leads of ECG signals. The ECG analyzer can, for example, execute the single channel noise discrimination process where the ECG data segment was recorded using one or more pairs of electrodes. Alternatively or additionally, the ECG analyzer can execute the dual channel noise discrimination process where the ECG data segment was recorded using two or more pairs of electrodes. For additional leads, the ECG analyzer can, for example, execute second, different instance of the single channel noise discrimination process along with a first instance of the single channel noise discrimination process.

In some examples, both the single channel noise discrimination process and the dual channel noise discrimination process are configured to transform each channel of ECG data within the ECG data segment into a baseline ECG representation. The baseline ECG representation, for example may be a time-varying form of the ECG data where fiducial peaks such as the R peaks and/or other ECG outliers are removed providing a residual signal as the baseline representation. In implementations, other fiducial peaks such as P, T, and U peaks may also be removed. Executing such a transformation can include, for example, dividing the channel of the ECG data segment into a plurality of sub-samples or portions and removing outliers that transgress a threshold from each portion. In some examples, such outliers may include ECG data points that are not representative of the patient's actual cardiac function. For example, the baseline noise may manifest at low frequencies, e.g., generally less than 0.5 Hz. In some examples, the baseline noise may be in a range from around less than 0.75 Hz to around less than 1 Hz. In examples, the baseline noise may be due to respiration artifact (e.g., chest wall movements due to breathing), perspiration changes to electrode impedance, or other patient movement activity.

Additionally or alternatively, in some examples, both the single channel noise discrimination process and the dual channel noise discrimination process are configured to fit the baseline representation to a function. In some examples, this function is a polynomial. The polynomial can be, for example, a third-degree polynomial.

In some examples, the noise discrimination processes use one or more coefficients of the function to determine whether the ECG data segment is noisy according to pre-determined criteria. For instance, where a coefficient of the function transgresses a threshold value, the noise discrimination processes can classify the ECG data segment as noisy. To produce the filtered collection of ECG data segments (the groomed ECG data sets), the ECG analyzer can, in some examples, create a second collection of ECG data segments that excludes any ECG data segments recorded as noisy.

In some examples, the dual channel noise discrimination process provides an additional level of filtering to increase the quality of the groomed collection of ECG data segments. For instance, in some examples, the dual channel noise discrimination process identifies QRS complexes in both channels, determines whether each QRS complex in the first channel as a matching QRS complex in the second channel, and calculates an average RR interval between QRS complexes for both channels. In these examples, the dual channel noise discrimination process records an ECG data segment as noisy where the ECG analyzer detects two or more QRS complexes in the first channel that do not have corresponding QRS complexes in the second channel and/or where the average RR interval of the first channel differs from the average RR interval of the second channel by more than a threshold amount.

In some examples, the collection of ECG data segments can be stored in ECG file formats that include not only raw and/or unprocessed ECG data but also associated ECG metrics (e.g., heart rate, heart rate variability, QRS duration, etc.) and associated metadata (patient identifier, patient demographic information, etc.) regarding the ECG data segments. For instance, in at least one example, the ECG analyzer can be configured to count the number of PVCs present within an ECG data segment. In this example, the ECG analyzer executes a PVC identification process. For example, PVC can be characterized by a long RR interval, followed by a short RR interval, followed by another long RR interval. The PVC identification process compares RR intervals present within the ECG data segment to identify compensatory pauses, which in turn, identify candidate PVCs. In examples, the PVC identification process further verifies that candidate PVCs are actual PVCs by comparing candidate QRS complexes to a template that represents a patient's normal heart beat morphology and by comparing the candidate QRS complexes to the morphology of other neighboring heart beats. In some examples where an ECG data segment comprises dual channels, the ECG analyzer further verifies its PVC counts by attempting to match PVCs identified in a first channel to PVCs identified in a second channel to verify temporal correspondence between the detected PVCs on both channels.

The ECG data segments that make up both the unfiltered and filtered ECG data collection can be recorded using a variety of medical devices. Such devices can include patient monitoring and/or treatment devices monitor that record various physiological or vital signals via one or more sensing electrodes or sensors that are coupled externally to a patient's skin. For example, a cardiac monitoring and/or treatment device can monitor and record electrocardiogram (ECG) signals via ECG sensing electrodes that are adapted for external attachment or coupling to the skin of the patient. These sensing electrodes acquire physiological signals in analog form that are descriptive of the physiology of the patient. Based upon further analysis of these physiological signals, various metrics such as ECG metrics can be determined or derived. For example, metrics such as heart rate, heart rate variability, heart rate turbulence, QRS duration, QT interval, premature ventricular contraction (PVC) count, and other similar metrics can be determined or derived from the physiological signals.

As noted herein, patient monitoring and treatment devices are used to monitor and record various physiological or vital signals for a patient and provide treatment to a patient when necessary. For patients at risk of a cardiac arrhythmia, specialized cardiac monitoring and/or treatment devices such as a cardiac event monitoring device, a wearable cardioverter defibrillator (WCD), or a hospital wearable defibrillator can be prescribed to and worn by the patient for an extended period of time. For example, a patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed a specialized cardiac monitoring and/or treatment device.

In some examples, the patient monitoring and treatment devices are used to monitor patients who are classified in accordance with heart failure classifications adopted by a physician's or hospital group, association, or other regulatory authority. For example, the ECG metrics derived from search devices can be used to monitor a patient's heart failure condition that may be worsening. For example, such authority may be the American College of Cardiology (ACC), the American Heart Association (AHA), and the New York heart Association (NYHA). For example, the patient monitoring and treatment devices can be prescribed to patients who fall under stages C or D in the ACC/AHA scheme. The stages of the ACC/AHA scheme follow.

Patients at risk for heart failure who have not yet developed structural heart changes (i.e. those with diabetes, those with coronary disease without prior infarct) are classified in Stage A patients. Stage A is considered pre-heart failure. In this stage, patients are monitored for signs of hypertension, diabetes, coronary artery disease, metabolic syndrome, a history of alcohol abuse, a history of rheumatic fever, a family history of cardiomyopathy, a history of taking drugs that can damage heart muscle, such as some cancer drugs.

Patients with structural heart disease (i.e. reduced ejection fraction, left ventricular hypertrophy, chamber enlargement) who have not yet developed symptoms of heart failure are classified in Stage B. Stage B is considered pre-heart failure. This means the patient has been diagnosed with at least systolic left ventricular dysfunction but may have never had symptoms of heart failure. Most people with Stage B heart failure may have an echocardiogram (echo) that shows an ejection fraction (EF) of 40% or less. This category can include people who have heart failure and reduced EF (HF-rEF) due to any cause.

Patients who have developed clinical heart failure are classified in Stage C. Stage C patients generally have been diagnosed with heart failure and currently or previously exhibited signs and symptoms of the condition. There are many possible symptoms of heart failure.

Patients with refractory heart failure requiring advanced intervention (i.e. biventricular pacemakers, left ventricular assist device, transplantation) are classified in Stage D. Patients with Stage D and reduced EF (HF-rEF patients) have advanced symptoms that generally do not get much better with treatment. This is usually considered a final stage of heart failure.

Additionally or alternatively, the patient monitoring and treatment device can be prescribed to patients who fall under Class III or IV of the NYHA. In the NYHA, Class I and Class II are considered mild. Class III is considered moderate and Class IV is severe.

In Class I there are no restrictions of physical activity. Patients generally don't complain of being overly tired or of experiencing shortness of breath. A patient is still able to control the disease. Regular exercise, limiting alcohol consumption, and eating healthy (with moderate sodium intake), are all actions that can be taken quite easily. High blood pressure will need to be treated. Quitting smoking is crucial.

With Class II heart failure, patients will feel slight restrictions with everyday physical actions like bending over or walking. They will be tired and shortness of breath may occur. Non-invasive surgical procedures like ACE-Inhibitors or Beta Blockers (depending on the patient), may be considered.

Class III heart failure patients experience definite limitations during physical activity. They may remain comfortable at rest, but most all physical activity will cause undue fatigue. Under physician care, their diet and exercise may be monitored. Diuretics, to combat water retention, may be prescribed.

Patients in Class IV heart failure are virtually unable to do any physical activity without discomfort. There may be significant signs of cardiac problems even while resting. Surgical options may be explored along with the same attention given to treatments in Classes I-III. Devices that provide ECG metrics using the techniques, systems, methods described herein that can be used to analyze a patient's heart failure condition. For example, the ECG metrics can be evaluated to determine that a patient from a plurality of patients who may be classified as Stage B may need to be re-classified as Stage C if the ECG metrics indicate a change (e.g., worsening) in the heart failure condition of the patient. Caregivers may then adjust their treatment plan accordingly.

In some examples, the patient monitoring and treatment device prescribed to the heart failure patient can be a WCD such as the LifeVest® Wearable Cardioverter Defibrillator from ZOLL Medical Corporation (Chelmsford, Mass.). As described in further detail below, such a device includes a garment that is configured to be worn about the torso of the patient. The garment can be configured to house various components such as ECG sensing electrodes and therapy electrodes. The components in the garment can be operably connected to a monitoring device that is configured to receive and process signals from the ECG sensing electrodes to determine a current cardiac condition of the patient and, if necessary, provide treatment to the patient using the therapy electrodes. Additionally, the monitoring device can be configured to operably couple to a remote computing device for transmission of collected data related to the patient for remote storage and analysis.

In implementations, dry ECG electrodes (e.g., such as those used in certain wearable cardioverter defibrillator applications) include polarizable electrodes where the capacitive coupling in the skin-electrode interface is modeled as a high impedance circuit. Such dry electrodes are susceptible to motion artifacts including baseline drift. One example of a dry ECG electrode is described further below with reference to FIG. 13.

As shown in FIG. 1A, an ECG processing system 100 can include multiple medical devices 110 and 120 operably coupled to a remote computing device, such as server 130, via a network 140. In certain implementations, each of the medical devices 110 and 120 can be prescribed to a particular patient. For example, as shown in FIG. 1A, medical device 110 can be prescribed to patient 111. The medical device 110 can include a sensor interface 112 operably coupled to one or more sensing electrodes that are configured to measure and collect physiological signals from the patient 111. The sensor interface 112 can be operably connected to a processor 113 that is configured to process the physiological signals received by the sensor interface. For example, the processor 113 can be configured to filter the physiological signals, convert the physiological signals into physiological data for transmission or further processing, and analyze the physiological data for an indication of the current cardiac condition of the patient 111. The processor 113 can be operably coupled to a network interface 114 that is, for example, operably coupled to a network 140. The network interface 114 can be configured to transfer the processed physiological data received from the processor 113 to a remote computing device such as server 130 via the network 140.

As further shown in FIG. 1A, the medical device 120 can be prescribed to a patient 121. The medical device 120 can include a sensor interface 122 operably coupled to one or more sensing electrodes that are configured to measure and collect physiological signals from the patient 121. The sensor interface 122 can be operably connected to a processor 123 that is configured to process the physiological signals received by the sensor interface. For example, the processor 123 can be configured to filter the physiological signals, convert the physiological signals to physiological data for transmission or further processing, and analyze the physiological data for an indication of the current cardiac condition of the patient 121. The processor 123 can be operably coupled to a network interface 124 that is, for example, operably coupled to a network 140. The network interface 124 can be configured to transfer the processed physiological data received from the processor 123 to a remote computing device such as server 130 via the network 140.

The server 130 can include a network interface that is configured to operably couple the server to network 140 and, by extension, each of medical devices 110 and 120. In such an example, information, such as patient physiological information, can be transferred from the medical devices 110 and 120 to the remote server via the network 140.

As shown in FIG. 1A, the server 130 can include various other components such as an application programming interface (API) layer 132, a processor 133, an ECG analyzer 134, a cardiac condition predictor 135, and a memory 136 that can be configured to store data such as ECG data segments 137 as collected from, for example, the medical devices 110 and 120. In some examples, the ECG data segments 137 can include various metadata or other similar fields to provide additional information. For example, elements of the ECG data segments 137 can include a first field allocated to store an amplitude value and a second field allocated to store a date and time value. However, it should be noted that these fields are shown by way of example only and additional data can be stored with the ECG data segments 137.

The API layer 132 can be configured to provide an interface between a program requesting information and a set of input arguments. For example, as shown in FIG. 1A, the API layer 132 can be configured to receive inputs as requested by the ECG analyzer 134, check the validity of the requested input arguments, and deliver the results to the calling program. In such an example, the processor 133 can be configured to provide specific instructions to the API layer 132 regarding the specific input arguments being requested. For example, the API layer can be configured to access and validate a set of input arguments such as those shown in TABLE 1 below:

TABLE 1

Sample API Input Arguments

| Argument | Description |
| --- | --- |
| ecgData | ECG data object |
| channelConfiguration | Single channel or dual channel mode |
| ecgSamplesPerSecond | ECG sampling rate |
| ecgBitDepth | Bits per sample |
| age | Age in years |
| gender | Male or female |
| cabg | Coronary artery bypass graft (CABG) |
| chf | Congestive Heart Failure (CHF) |
| hcm | Hypertrophic cardiomyopathy (HCM) |
| myocardialInfarction | Myocardial Infarction |
| vtOrVf | VT or VF [sustained or non-sustained] |
| icdExplant | Explant of ICD |

Referring again to FIG. 1A, the ECG analyzer 134 can be implemented as a processing device or as a module configured to be executed by, for example, the processor 133. However, it should be noted that the ECG analyzer 134 is shown in the server 130 and implemented by processor 133 by way of example only. In certain implementations, the ECG analyzer can be a processing device or a module integrated into one or both of medical device 110 and medical device 120. For example, the ECG analyzer can be implemented as a module configured to be executed by processor 113 of medical device 110. Medical device 120 can be similar configured with a local ECG analyzer 134 configured to be executed by processor 123.

The ECG analyzer 134 can be configured to perform a quality assessment of a received ECG signal and to compute one or more ECG metrics from raw ECG input signals. For example, the ECG analyzer can be configured to compute one or more ECG metrics as shown in TABLE 2 below:

TABLE 2

Example ECG Metrics

| Metric | | Description |
| --- | --- | --- |
| Heart Rate | $HR_{avg}$ | Average heart rate |
| | $HR_{min}$ | Minimum heart rate |
| | $HR_{max}$ | Maximum heart rate |
| Heart Rate Variability | $NN_{avg}$ | Average normal-to-normal interval in seconds |
| | $NN_{min}$ | Minimum normal-to-normal interval in seconds |
| | $NN_{max}$ | Maximum normal-to-normal interval in seconds |
| | $NN_{sd}$ | Standard deviation of normal-to-normal intervals in seconds |
| | RMS | Square root of the mean squared difference of successive normal-to-normal intervals measured in seconds |
| | NN50 | Number of successive normal-to-normal intervals greater than 50 ms per minute. |
| | pNN50 | Percentage of normal-to-normal intervals greater than 50 ms per minute. |
| Heart Rate Turbulence | TO | Turbulence Onset |
| | TS | Turbulence Slope |
| QRS Duration | $QRS_{med}$ | Median QRS duration |
| | $QRS_{sd}$ | Standard deviation of QRS duration |
| QTc Interval | $QTc_{med}$ | Median QT interval corrected by Bazett's formula |
| | $QTc_{sd}$ | Standard deviation of QT intervals corrected by Bazett's formula |
| PVCs | $PVC_{count}$ | Number of PVCs |
| | nsvtCount | Number of consecutive 4-beat sequences of PVCs |

The ECG analyzer can output one or more ECG metrics to, for example the cardiac condition predictor 135 for further analysis.

As further shown in FIG. 1A, the server 130 can also include a memory 136 configured to store various information such as the ECG data segments 137. In certain implementations, the ECG analyzer 134 can be configured to operate as a single or dual channel analyzer configured to determine noise present in one or more ECG signals. Depending upon the outcome of the noise determination, ECG analyzer 134 can be configured to store at least a portion of the ECG signal as an ECG data segment 137 in memory 136. If the ECG analyzer 134 determines that the ECG signal is too noisy for further analysis, the ECG signal can be discarded or stored in another location. If the ECG analyzer 134 determines that the ECG signal satisfies a noise threshold, at least a portion of the ECG signal can be stored in the memory 136. For example, the ECG data segments 137 can include ECG data segments extracted from an ECG strip, the segments having an average length of about 15 seconds, about 30 seconds, about 45 seconds, about 60 seconds, about 90 seconds, about 120 seconds, about 150 seconds, about 180 seconds, about 5 minutes, about 10 minutes, and about 15 minutes. Additional detail regarding the operation of the ECG analyzer is provided in the discussions of FIGS. 4A-8 below.

As further shown in FIG. 1A, the system 100 can further include a computing device 145 operably coupled to the network 140 can configured to communicate with one or more of the medical devices 110 and 120, and the server 130. In some examples, the computing device 145 can be associated with a healthcare professional 146. The healthcare professional 146 can use the computing device 145 to access, for example, information determined by the cardiac condition predictor 135 for review and/or further analysis.

Figure 1B:
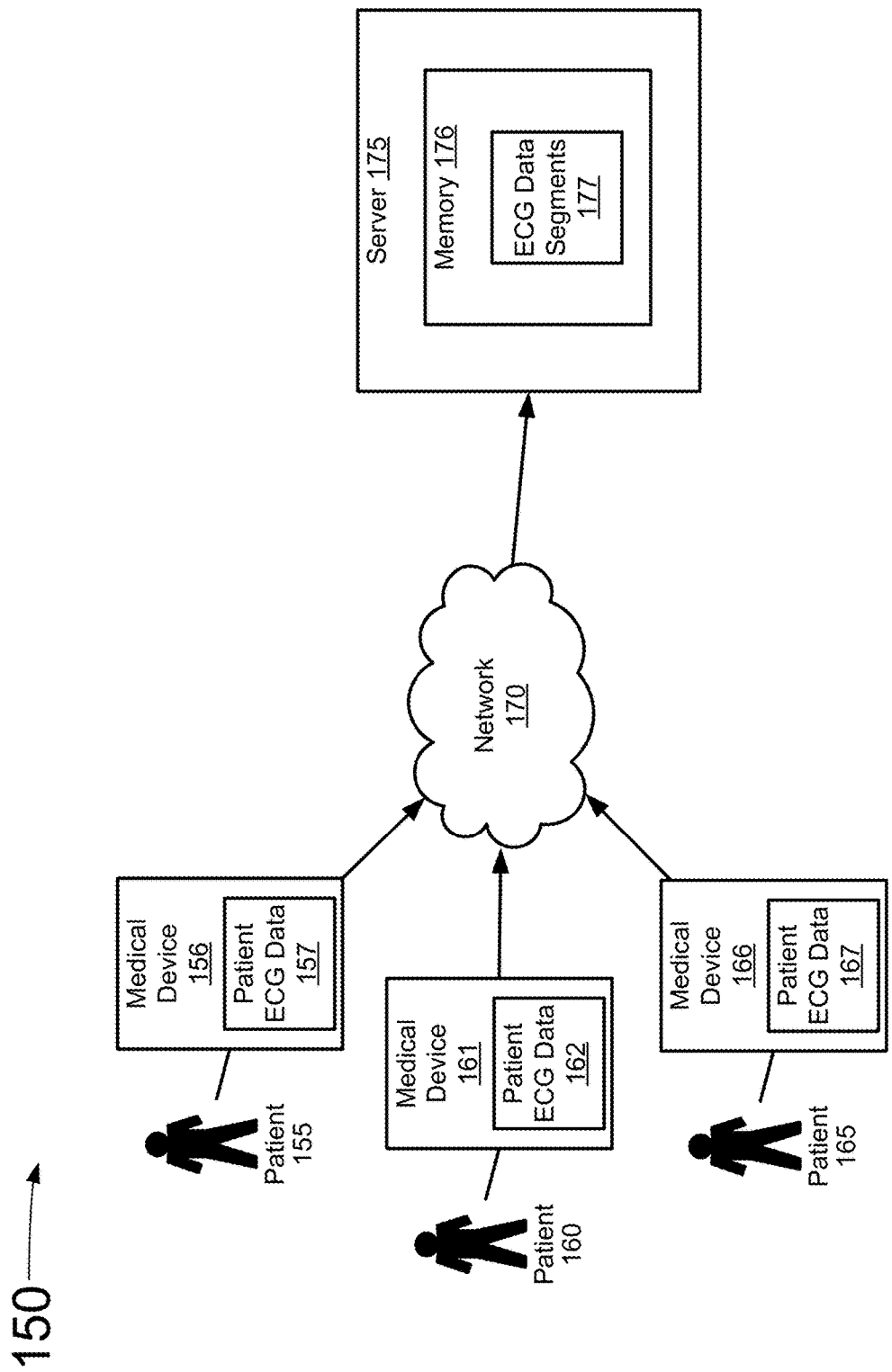
FIG. 1B depicts an overview of a system for collecting information from multiple patients, in accordance with an example of the present disclosure.

In certain examples, a system such as system 100 shown in FIG. 1A can be configured to collect data from multiple patients. For example, as shown in FIG. 1B, a system 150 can be configured to collect patient data from a sample population of patients 155, 160, and 165. For example, a patient 155 from such a patient population can be prescribed a medical device 156 that is configured to monitor and record, for example, ECG data for the patient 155. The medical device 156 can be configured to store the patient ECG data 157 for a particular time period (e.g., 24 hours, 48 hours, 1 week, 2 weeks, 30 days, 3 months, or more). During, or at the end of the monitoring time period, the medical device 156 can be configured to transmit the patient ECG data 157 to a remote server 175 via a network 170. The server 175 can be configured to process the patient ECG data 157 as described herein, and store at least a portion of the patient ECG data in memory 176 as one or more ECG data segments 177.

Similarly, the patient 160 can be prescribed a medical device 161 that is configured to monitor and record, for example, ECG data for patient 160. The medical device 161 can be configured to store the patient ECG data 162 for a particular time period. During, or at the end of the time period, the medical device 161 can be configured to transmit the patient ECG data 162 to the remote server 175 via the network 170. The server 175 can be configured to process the patient ECG data 162 as described herein, and store at least a portion of the patient ECG data in memory 176 as one or more ECG data segments 177.

As further shown in FIG. 1B, the patient 165 can be prescribed a medical device 166 that is configured to monitor and record, for example, ECG data for patient 165. The medical device 166 can be configured to store the patient ECG data 167 for a particular time period. During, or at the end of the time period, the medical device 166 can be configured to transmit the patient ECG data 167 to the remote server 175 via the network 170. The server 175 can be configured to process the patient ECG data 167 as described herein, and store at least a portion of the patient ECG data in memory 176 as one or more ECG data segments 177.

It should be noted that three patients, patients 155, 160 and 165, are shown in FIG. 1B by way of example only. In actual practice, a sample patient population of collected ECG data can include any number of patients. For example, a sample patient population can include ECG data collected from hundreds or thousands of patients.

Figure 1C:
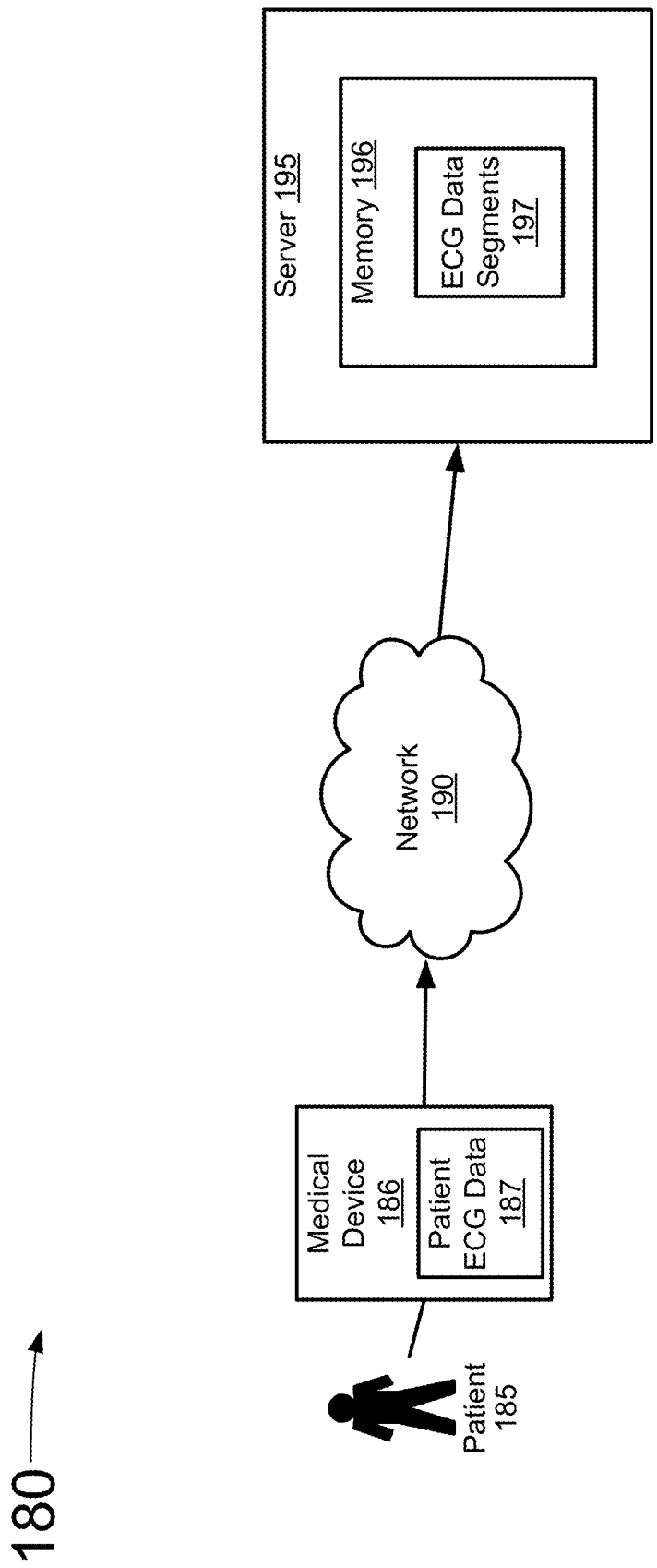
FIG. 1C depicts an overview of a system for collecting information from a single patient, in accordance with an example of the present disclosure.

In some implementations, a physician or other healthcare worker may want to analyze ECG data received from a single patient. In such an example, the physician may want to analyze trends in cardiac activity for the single patient. As shown in FIG. 1C, a system 180 can be configured to collect patient data from a single patient 185. The patient 185 can be prescribed a medical device 186 that is configured to monitor and record, for example, ECG data for patient 185. The medical device 186 can be configured to store the patient ECG data 187 for a particular time period. During, or at the end of the time period, the medical device 186 can be configured to transmit the patient ECG data 187 to a remote server 195 via a network 190. The server 195 can be configured to process the patient ECG data 187 as described herein, and store at least a portion of the patient ECG data in memory 196 as one or more ECG data segments 197.

In such a system as system 180 as shown in FIG. 1C, the requesting physician can access the ECG data segments 197 as stored in the server 195 and further analyze the data for the single patient 185.

Figure 2:
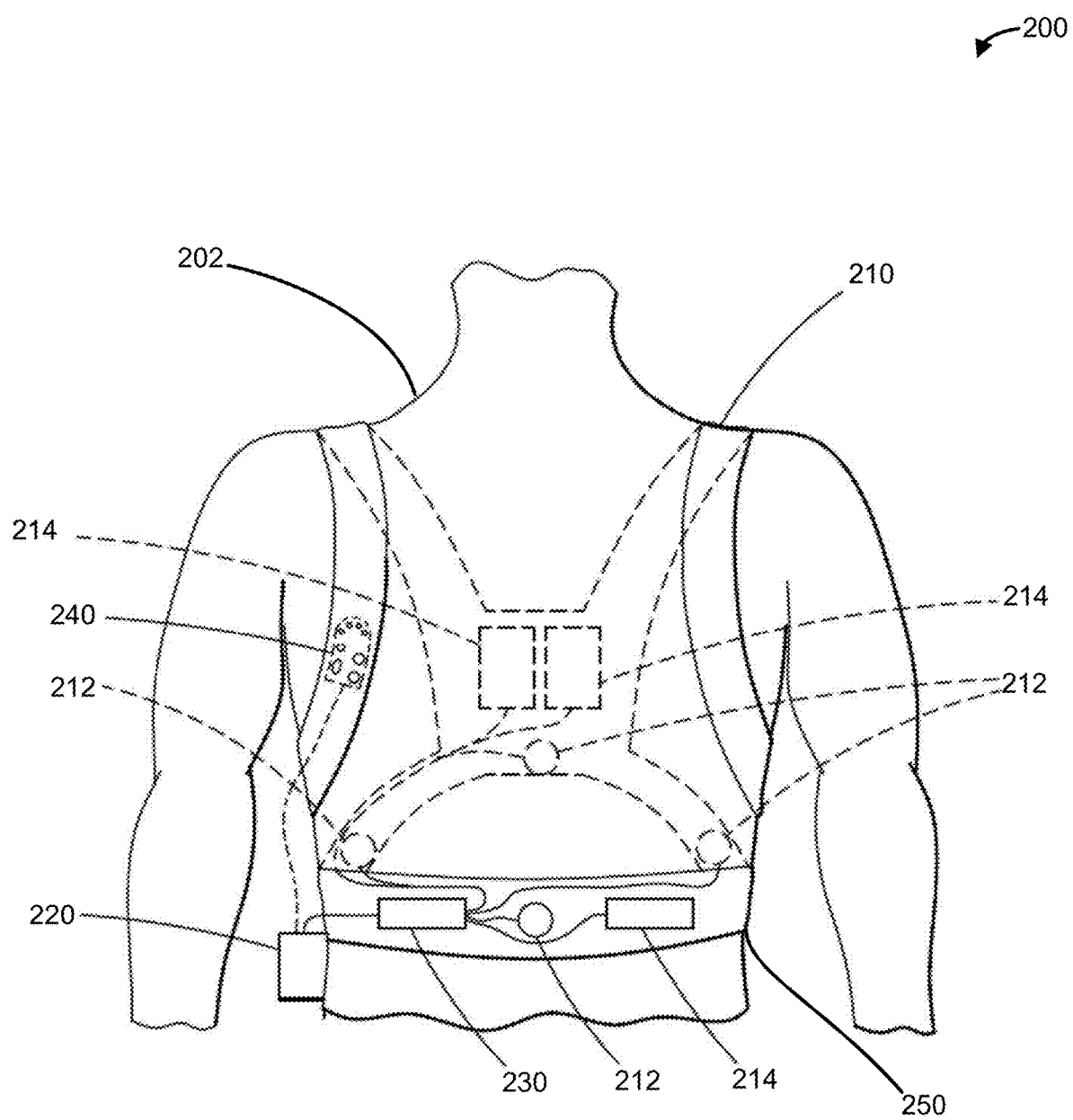
FIG. 2 depicts a sample ambulatory medical device configured to collect patent information, in accordance with an example of the present disclosure.

An ECG processing system, such as the ECG processing system 100, can process ECG data originated from a wide variety of medical devices in accordance with the various examples disclosed herein. Examples of these medical device include internal/implantable medical devices (e.g., pacemakers and/or implantable cardioverter defibrillators), mobile cardiac telemetry devices, and hospital medical monitors, among other medical devices. FIG. 2 illustrates an example medical device 200 that can provide ECG data for processing by an ECG processing system. The medical device 200 is external, ambulatory, and wearable by a patient 202, and configured to patient physiological data as described herein. For example, the medical device 200 can be a non-invasive medical device configured to be located substantially external to the patient. Such a medical device 200 can be, for example, an ambulatory medical device that is capable of and designed for moving with the patient as the patient goes about his or her daily routine. For example, the medical device 200 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 200 can include one or more of the following: a garment 210, one or more sensing electrodes 212, one or more therapy electrodes 214a and 214b (collectively referred to herein as therapy electrodes 214), a medical device controller 220, a connection pod 230, a patient interface pod 240, a belt 250, or any combination of these. In some examples, at least some of the components of the medical device 200 can be configured to be affixed to the garment 210 (or in some examples, permanently integrated into the garment 210), which can be worn about the patient's torso.

The medical device controller 220 can be operatively coupled to the sensing electrodes 212, which can be affixed to the garment 210, e.g., assembled into the garment 210 or removably attached to the garment, e.g., using hook and loop fasteners. In some implementations, the sensing electrodes 212 can be permanently integrated into the garment 210. The medical device controller 220 can be operatively coupled to the therapy electrodes 214. For example, the therapy electrodes 214 can also be assembled into the garment 210, removably attached to the garment, or, in some implementations, the therapy electrodes can be permanently integrated into the garment.

Component configurations other than those shown in FIG. 2 are possible. For example, the sensing electrodes 212 can be configured to be attached at various positions about the body of the patient 202. The sensing electrodes 212 can be operatively coupled to the medical device controller 220 through the connection pod 230. In some implementations, the sensing electrodes 212 can be adhesively attached to the patient 202. In some implementations, the sensing electrodes 212 and at least one of the therapy electrodes 214 can be included on a single integrated patch and adhesively applied to the patient's body.

The sensing electrodes 212 can be configured to detect one or more physiological signals such as cardiac signals. Examples of such signals include ECG signals and/or other sensed cardiac physiological signals from the patient. In certain examples, as described herein, the sensing electrodes 212 can include additional components such as accelerometers, acoustic signal detecting devices, and other measuring devices for recording additional parameters. For example, the sensing electrodes 212 can also be configured to detect other types of patient physiological parameters and acoustic signals, such as tissue fluid levels, cardio-vibrations, lung vibrations, respiration vibrations, patient movement, etc.

In some examples, the therapy electrodes 214 can also be configured to include sensors configured to detect ECG signals as well as other physiological signals of the patient. The connection pod 230 can, in some examples, include a signal processor configured to amplify, filter, and digitize these cardiac signals prior to transmitting the cardiac signals to the medical device controller 220. One or more of the therapy electrodes 214 can be configured to deliver one or more therapeutic defibrillating shocks to the body of the patient 202 when the medical device 200 determines that such treatment is warranted based on the signals detected by the digital sensing electrodes 212 and processed by the medical device controller 220. Example therapy electrodes 214 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 214 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 3:
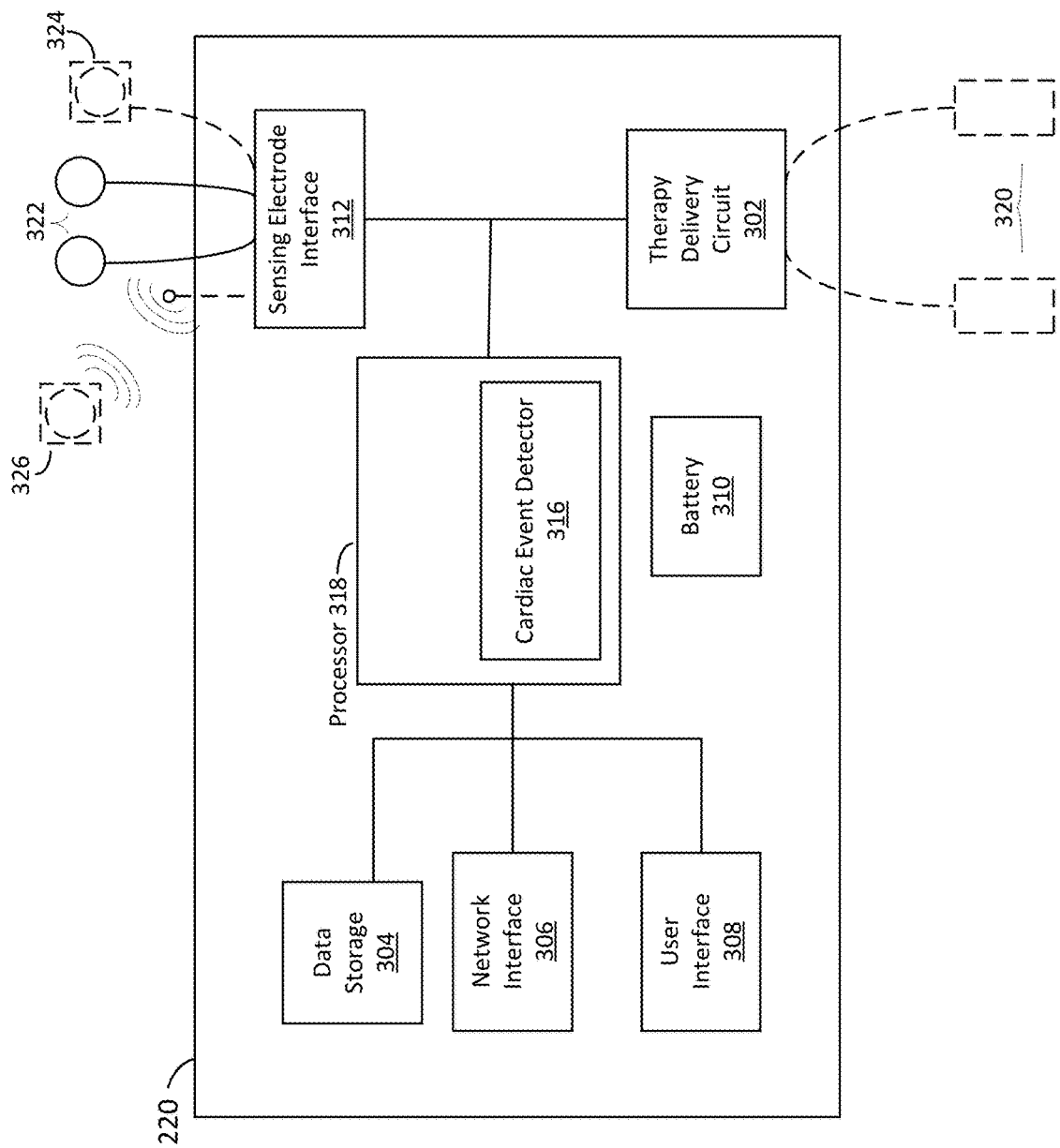
FIG. 3 depicts a schematic view of a sample controller for an ambulatory medical device that includes digital sensing electrodes, in accordance with an example of the present disclosure.

FIG. 3 illustrates an example component-level view of the medical device controller 220 as described above in regard to FIG. 2. As shown in FIG. 3, the medical device controller 220 can include a therapy delivery circuitry 302, a data storage 304, a network interface 306, a user interface 308, at least one battery 310, a sensor interface 312, a cardiac event detector 316, and least one processor 318.

In some examples, the patient monitoring medical device can include a medical device controller 220 that includes like components as those described above but does not include the therapy delivery circuitry 302 (shown in dotted lines).

The therapy delivery circuitry 302 can be coupled to one or more electrodes 320 configured to provide therapy to the patient. For example, the therapy delivery circuitry 302 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 318) to provide, for example, at least one therapeutic shock to the patient including one or more pacing or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 302 can be configured to perform the switching and pulse delivery operations, e.g., under control of the processor 318. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 304 can include one or more of non-transitory computer readable media, such as flash memory, solid state memory, magnetic memory, optical memory, cache memory, combinations thereof, and others. The data storage 304 can be configured to store executable instructions and data used for operation of the medical device controller 220. In certain examples, the data storage can include executable instructions that, when executed, are configured to cause the processor 318 to perform one or more operations.

In some examples, the network interface 306 can facilitate the communication of information between the medical device controller 220 and one or more other devices or entities over a communications network. For example, where the medical device controller 220 is included in an ambulatory medical device, the network interface 306 can be configured to communicate with a remote computing device such as a remote server or other similar computing device. The network interface 306 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 220. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 308 can include one or more physical interface devices such as input devices, output devices, and combination input/output devices and a software stack configured to drive operation of the devices. These user interface elements can render visual, audio, and/or tactile content. Thus, the user interface 308 can receive input or provide output, thereby enabling a user to interact with the medical device controller 220.

The medical device controller 220 can also include at least one battery 310 configured to provide power to one or more components integrated in the medical device controller 220. The battery 310 can include a rechargeable multi-cell battery pack. In one example implementation, the battery 310 can include three or more 2200 mAh lithium ion cells that provide electrical power to the other device components within the medical device controller 220. For example, the battery 310 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 220.

The sensor interface 312 can include physiological signal circuitry that is coupled to one or more sensors configured to monitor one or more physiological parameters of the patient. As shown, the sensors can be coupled to the medical device controller 220 via a wired or wireless connection. The sensors can include one or more sensing electrodes 322, vibration sensor 324, and tissue fluid monitors 326 (e.g., based on ultra-wide band radiofrequency devices). In some implementations, the sensors can include a plurality of conventional ECG sensing electrodes in addition to digital sensing electrodes.

The sensing electrodes 322 can be configured to monitor a patient's ECG information. For example, by design, the digital sensing electrodes 322 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 322 can be used with an electrolytic gel dispersed between the electrode surface and the patient's skin. In certain implementations, the electrodes 322 can be dry electrodes that do not need an electrolytic material. As an example, such a dry electrode can be based on tantalum metal and having a tantalum pentoxide coating as is described above. Such dry electrodes can be more comfortable for long term monitoring applications.

Figure 13:
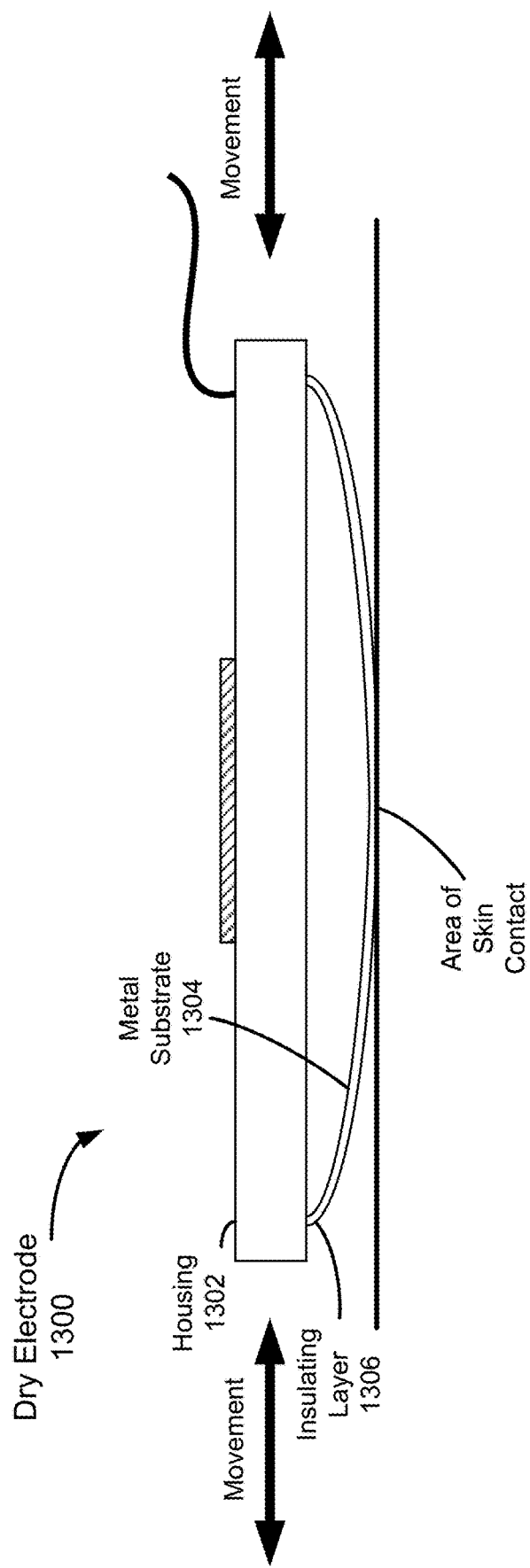
FIG. 13 depicts a dry electrode that can be used to collect ECG signals, in accordance with an example of the present disclosure.

FIG. 13 illustrates a dry ECG electrode 1300. As shown in FIG. 13, the electrode 1300 includes a housing 1302, a metal substrate 1304, and an insulating layer 1306. In some examples, the electrode 1300 is a polarizable electrode where the capacitive coupling in the skin-electrode interface is modeled as a high impedance circuit. In examples, the insulating layer may be tantalum pentoxide layer over a tantalum metal substrate 1304. In the electrode 1300, to achieve strong capacitive coupling, an area of contact with the patient's skin is greater relative to traditional non-polarizable electrodes (Ag/AgCl electrodes, for example). The electrode 1300 is susceptible to motion artifacts including baseline drift. In particular, as a result of movements of the electrode on the patient's skin and time-varying pressure of the electrode against the skin, the area of contact with the patient's skin continually changes. This affects the capacitance value in the high impedance circuit resulting in a time-varying charge (or displacement current) flowing across the interface. An ECG signal is taken across the electrode coupled to another electrode before being high pass coupled to a front-end circuit, consequently introducing a baseline drift in the ECG signal.

Referring back to FIG. 3, the vibration sensors 324 be configured to detect cardiac or pulmonary vibration information. For example, the vibration sensors 324 can detect a patient's heart valve vibration information. For example, the vibration sensors 324 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), percentage of EMAT (% EMAT), systolic dysfunction index (SDI), and left ventricular systolic time (LVST). The vibration sensors 324 can also be configured to detect heart wall motion, for instance, by placement of the sensor in the region of the apical beat. The vibration sensors 324 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 324 can also include a multi-channel accelerometer, for example, a three-channel accelerometer configured to sense movement in each of three orthogonal axes such that patient movement/body position can be detected and correlated to detected cardio-vibrations information. The vibration sensors 324 can transmit information descriptive of the cardio-vibrations information to the sensor interface 312 for subsequent analysis.

The tissue fluid monitors 326 can use radio frequency (RF) based techniques to assess fluid levels and accumulation in a patient's body tissue. For example, the tissue fluid monitors 326 can be configured to measure fluid content in the lungs, typically for diagnosis and follow-up of pulmonary edema or lung congestion in heart failure patients. The tissue fluid monitors 326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 326 can transmit information descriptive of the tissue fluid levels to the sensor interface 312 for subsequent analysis.

In certain implementations, the cardiac event detector 316 can be configured to monitor a patient's ECG signal for an occurrence of a cardiac event such as an arrhythmia or other similar cardiac event. The cardiac event detector can be configured to operate in concert with the processor 318 to execute one or more algorithms to process received ECG signals from, for example, the sensing electrodes 322 and determine the likelihood that a patient is experiencing a cardiac event. The cardiac event detector 316 can be implemented using hardware or a combination of hardware and software. For instance, in some examples, cardiac event detector 316 can be implemented as a software component that is stored within the data storage 304 and executed by the processor 318. In this example, the instructions included in the cardiac event detector 316 can cause the processor 318 to perform one or more algorithms for analyzing a received ECG signal to determine whether an adverse cardiac event is occurring. In other examples, the cardiac event detector 316 can be an application-specific integrated circuit (ASIC) that is coupled to the processor 318 and configured to monitor ECG signals for adverse cardiac event occurrences. Thus, examples of the cardiac event detector 316 are not limited to a particular hardware or software implementation.

In some implementations, the processor 318 includes one or more processors (or one or more processor cores) that each are configured to perform a series of instructions that result in manipulated data and/or control the operation of the other components of the medical device controller 220. In some implementations, when executing a specific process (e.g., cardiac monitoring), the processor 318 can be configured to make specific logic-based determinations based on input data received and be further configured to provide one or more outputs that can be used to control or otherwise inform subsequent processing to be carried out by the processor 318 and/or other processors or circuitry with which processor 318 is communicatively coupled. Thus, the processor 318 reacts to specific input stimulus in a specific way and generates a corresponding output based on that input stimulus. In some example cases, the processor 318 can proceed through a sequence of logical transitions in which various internal register states and/or other bit cell states internal or external to the processor 318 can be set to logic high or logic low. As referred to herein, the processor 318 can be configured to execute a function where software is stored in a data store coupled to the processor 318, the software being configured to cause the processor 318 to proceed through a sequence of various logic decisions that result in the function being executed. The various components that are described herein as being executable by the processor 318 can be implemented in various forms of specialized hardware, software, or a combination thereof.

For example, the processor 318 can be a digital signal processor (DSP) such as a 24-bit DSP. The processor 318 can be a multi-core processor, e.g., having two or more processing cores. The processor 318 can be an Advanced RISC Machine (ARM) processor such as a 32-bit ARM processor or a 64-bit ARM processor. The processor 318 can execute an embedded operating system, and include services provided by the operating system that can be used for file system manipulation, display & audio generation, basic networking, firewalling, data encryption and communications. In some examples, the processor 318 can be configured to process ECG signals and execute the noise detection and PVC detection processes and algorithms as described herein.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more megaohms). This high source impedance signal is processed and transmitted to a monitoring device such as processor 318 of the controller 220 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 4A:
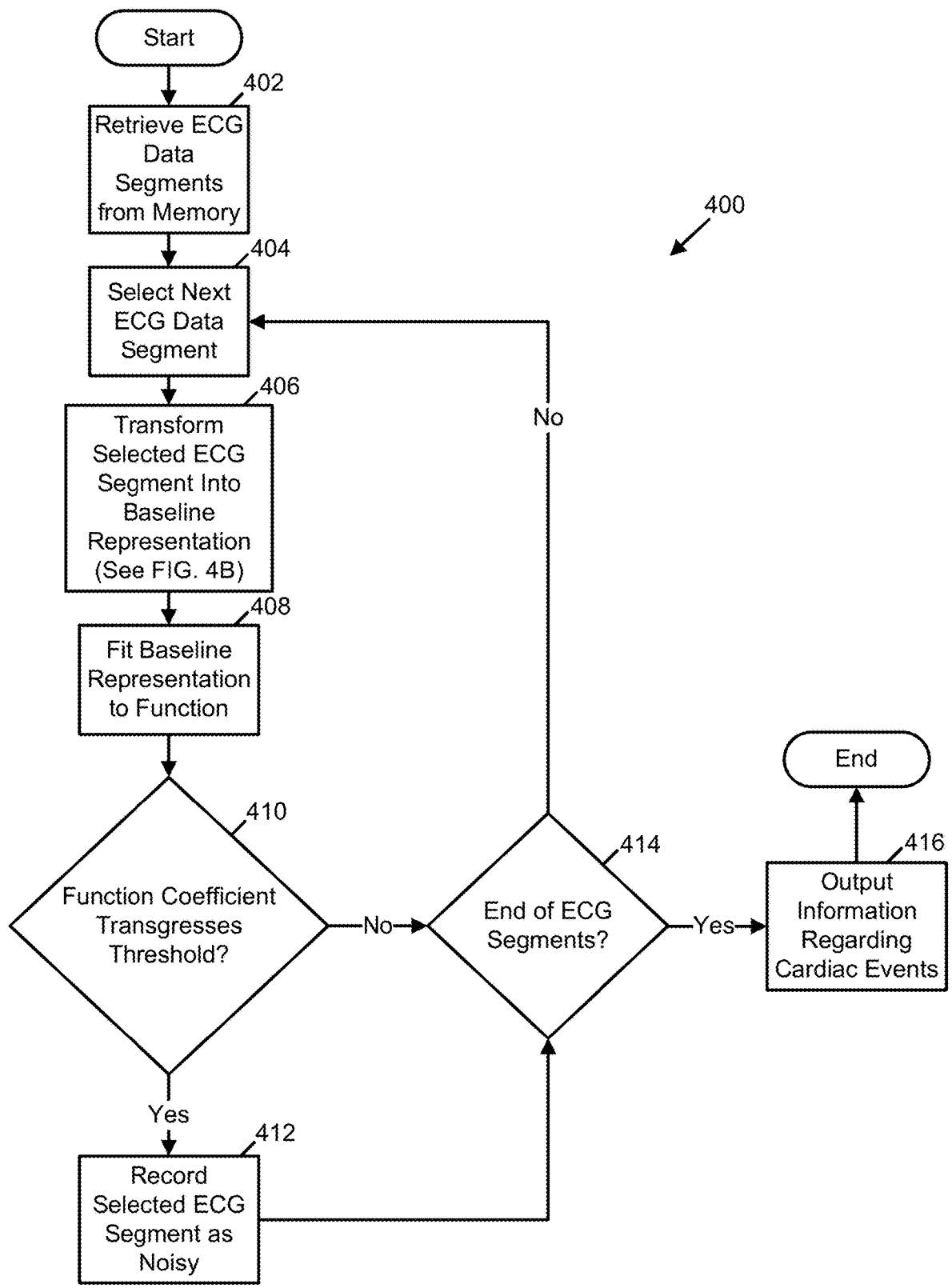
FIG. 4A depicts a sample flow for a single channel noise discrimination process, in accordance with an example of the present disclosure.

As noted above, an ECG analyzer can be configured to process received ECG data to determine if the ECG data is noisy or otherwise transgresses a particular threshold for signal quality. Depending upon the configuration of the ECG analyzer, the ECG analyzer can be configured to operate in a single or dual channel mode. FIG. 4A illustrates a sample process 400 for analyzing the ECG data in a single channel mode.

As shown in FIG. 4A, a processing device such as processor 133 as described above or, in certain implementations, the ECG analyzer 134, can implement the single channel process 400 by retrieving 402 ECG data segments from memory. For example, the processor 133 as shown in FIG. 1A can be configured to retrieve one or more ECG data segments 137 from the memory 136.

Figure 4B:
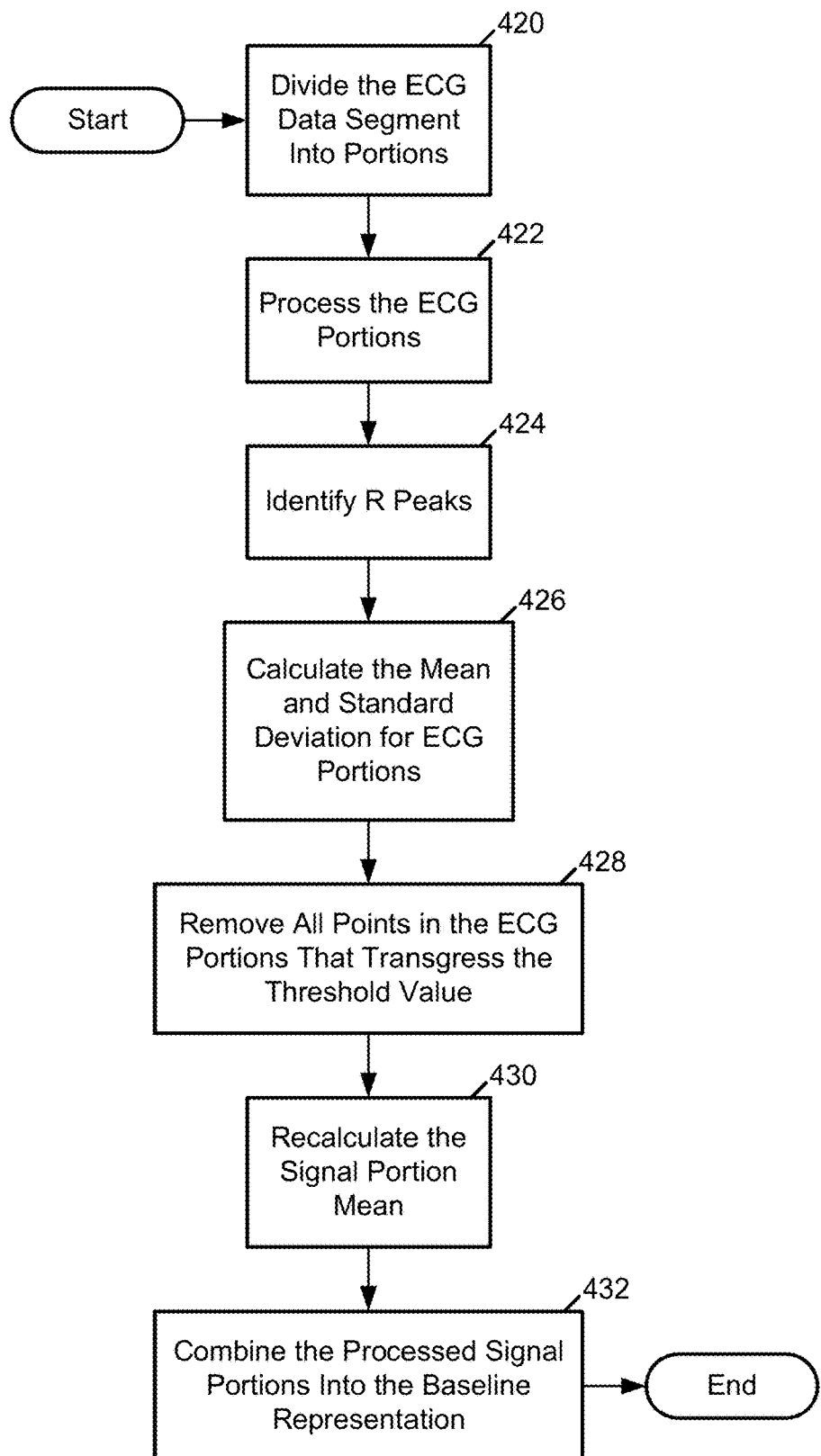
FIG. 4B depict a sample implementation of one or more process steps as shown in FIG. 4A, in accordance with an example of the present disclosure.

Referring again to FIG. 4A, the processor can select 404 a next ECG data segment from the retrieved data segments. If the process has just initialized, the processor can be configured to select 404 the first ECG data segment retrieved from memory. The processor can transform 406 the selected ECG data segment into a baseline representation. A sample process for transforming 406 the selected ECG data segment into a baseline representation is shown in FIG. 4B. For example, as shown in FIG. 4B, transforming 406 the selected ECG data segment into a baseline representation can include dividing 420 the ECG data segment into portions having a certain time period. For example, the processor can be configured to divide 420 the ECG data segment into a number of subsample portions having a time period spanning between about 2 second and about 8 seconds. In a certain implementation, the processor can divide 420 the ECG data segment into 4 second portions. For each of the portions, the processor can filter or otherwise process 422 the portions to remove ECG data contained within the portions that transgresses a particular threshold value. For example, for each portion, the processor can identify 424 the R peaks in the QRS complexes. For each R peak, the processor can calculate 426 the mean and standard deviation including the R peaks. For example, the processor can determine a mean for the ECG data for each of the portions, determine the standard deviation of the ECG data for each of the portions, and calculate the threshold value based upon the mean and the standard deviation. For example, the threshold value can be calculated such that any portion of the ECG data identified as outliers as compared to the mean and standard deviation are excluded from the ECG data. Although means and standard deviations are described herein, other statistical measures can be used to make such calculations. For example, instead of the mean, a median or mode or other representative value for the various ECG data points may be regarded.

Referring back to FIG. 4B, the processor can remove 428 all points that transgress the threshold. For example, the processor can be configured to remove all points lying more than 2 standard deviations from the mean, thereby effectively removing the R peaks from the ECG data segment portions. The processor can then recalculate 430 the mean amplitude for the portion. The processor can then combine 432 the points representing the mean amplitudes for the processed portion as the baseline representation. Although the process in FIG. 4B is shown to be removing only R peaks, the process can be adapted to also remove other fiducial ECG peaks such as P, T, or U peaks using a similar threshold determination process as described above for R peaks.

Referring again to process 400 as shown in FIG. 4A, the processor can fit 408 the baseline representation to a function. In certain implementations, the function can include at least one coefficient. For example, the processor can fit the baseline representation to a polynomial function such as a third-degree polynomial function. For example, the resulting points representing a mean amplitude in each portion are fit using a linear regression to a third-degree polynomial. In such an example, the coefficient can be a coefficient of a first-degree monomial of the third-degree polynomial. A polynomial function is shown by way of example only. Alternatively or in addition, other functions can be used. For example, a logarithm, exponential, hyperbolic, power, or trigonometric function can be used alone or in combination with a polynomial function.

Figure 9:
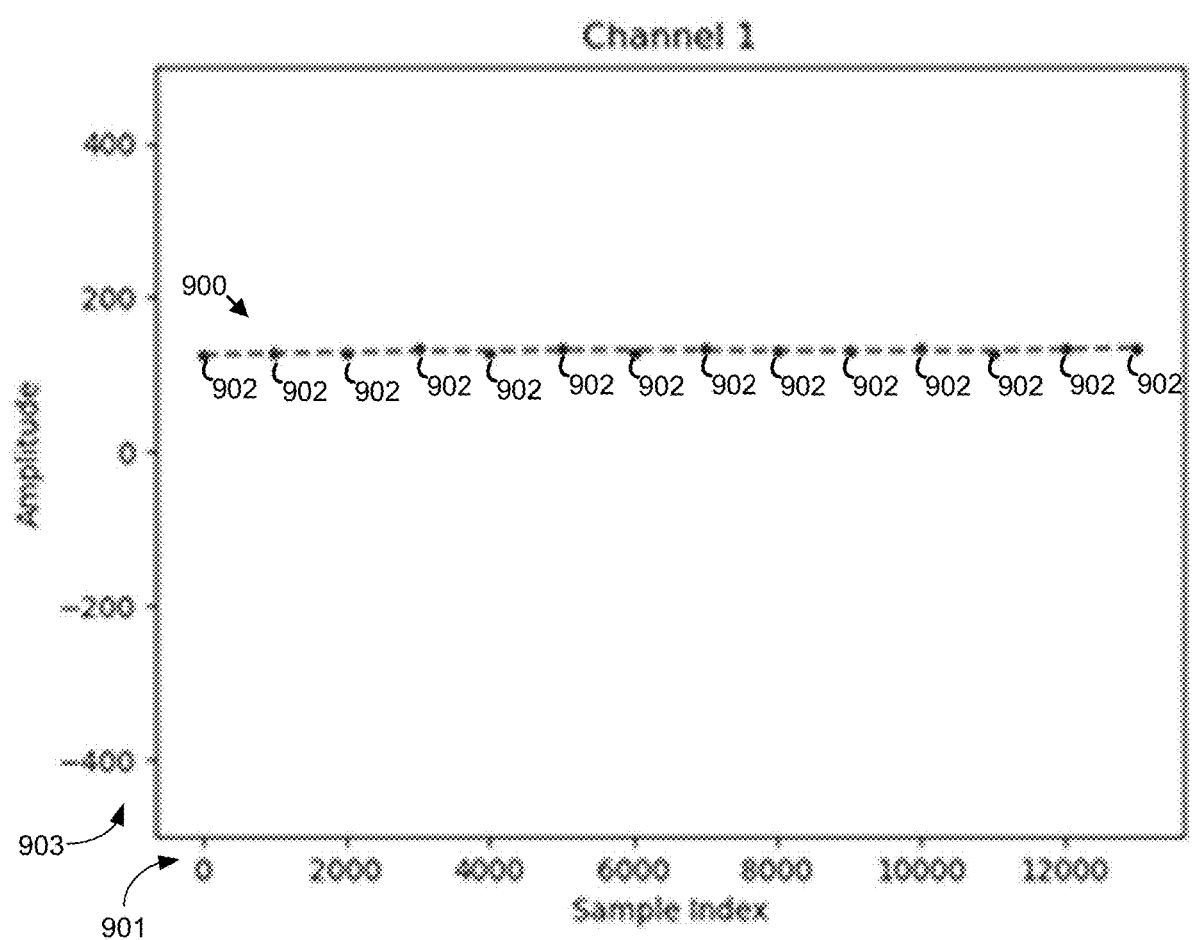
FIG. 9 depicts an example polynomial fit to an ECG sample, in accordance with an example of the present disclosure.

FIG. 9 graphically illustrates one example of a baseline representation of an ECG data segment when fit with a third-degree polynomial. In the example, each dot 902 represents the mean amplitude of a 4 second subsample. The x-axis 901 represents sample index values for raw ECG data, and the y-axis 903 represents amplitude values corresponding to the ECG data. As shown, the graphical representation of the third-degree polynomial 900 fits the sequence of mean amplitude dots 902 tightly. This tight fit indicates that the polynomial 900 characterizes the sequences of mean amplitudes well, and thus can be used to assess whether the mean amplitudes 902 contain baseline drift.

Figure 10:
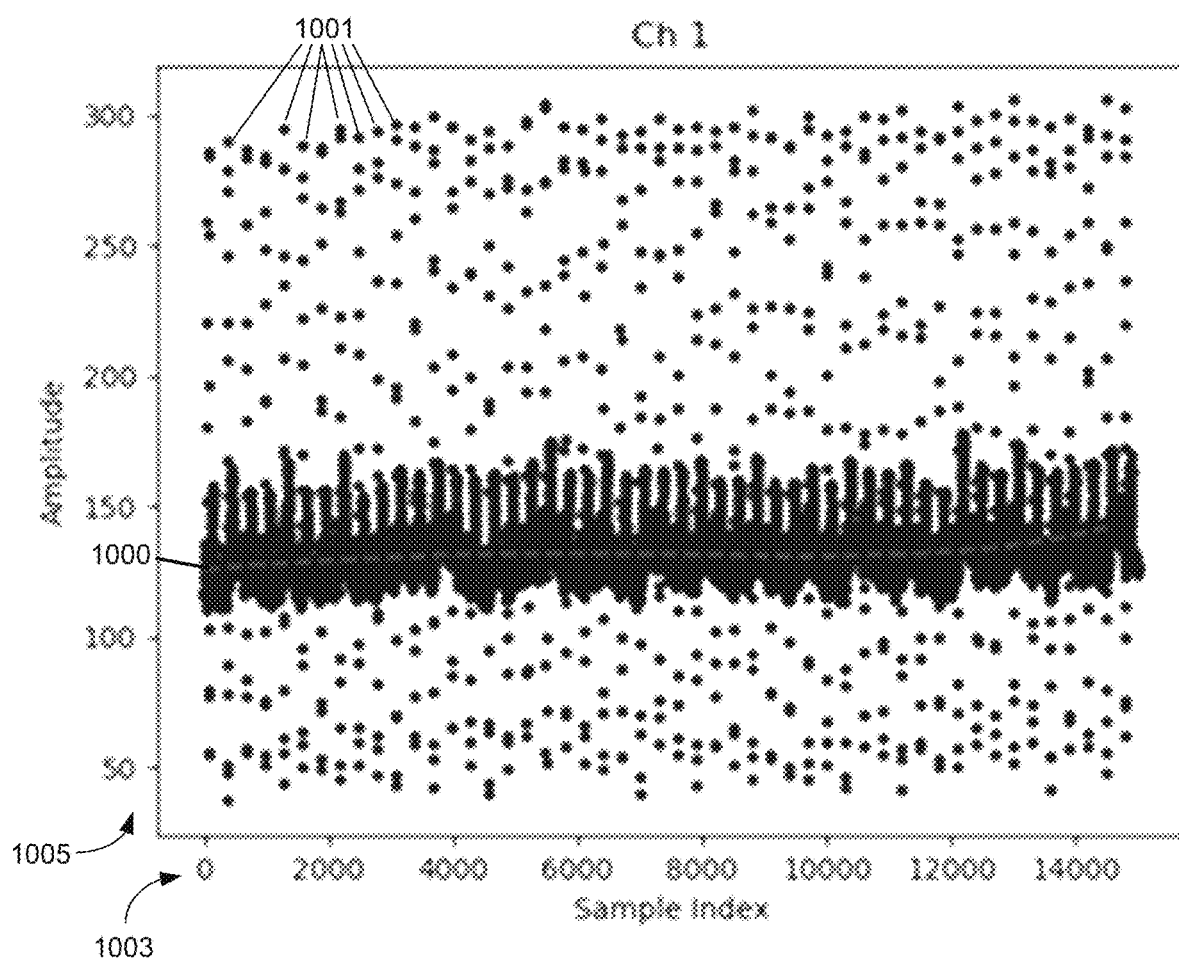
FIG. 10 depicts another example polynomial fit to an ECG sample, in accordance with an example of the present disclosure.

FIG. 10 provides another view of an ECG data segment. Each dot 1001 represents a raw ECG data sample. The x-axis 1003 represents sample index for raw ECG data, and the y-axis 1005 represents amplitude values corresponding to the raw ECG data. FIG. 10 illustrates a graphical representation of a polynomial 1000 fit to a baseline representation of the ECG data segment within the context of raw ECG signals used to generate the ECG data segment. As can be seen in FIG. 10, the polynomial 1000 is disposed near the center of the raw ECG signal dots, illustrating that the isoelectric levels of the ECG signals are well modeled. It should be noted that, while only a portion of the dots as shown in FIG. 10 are labeled as 1001, each dot included in FIG. 10 represents a raw ECG data sample.

The processor can determine 410 if the function coefficient transgresses a particular threshold. For illustration, example values of such coefficients are now described. In implementations, different numeric values may be used. In implementations, the numeric ranges shown be can be transformed to other numeric ranges (e.g., a range of −1.0 to 1.0 can be transformed to a range of 0 to 100). For example, the function as selected above to which the baseline representation is fit can be configured to output a coefficient having a value between −1.0 and 1.0. In such an example, the range of acceptable threshold values can range from about −0.5 and 0.5. As such, a coefficient value that transgresses this range can be considered representative of noisy ECG data.

Figure 11:
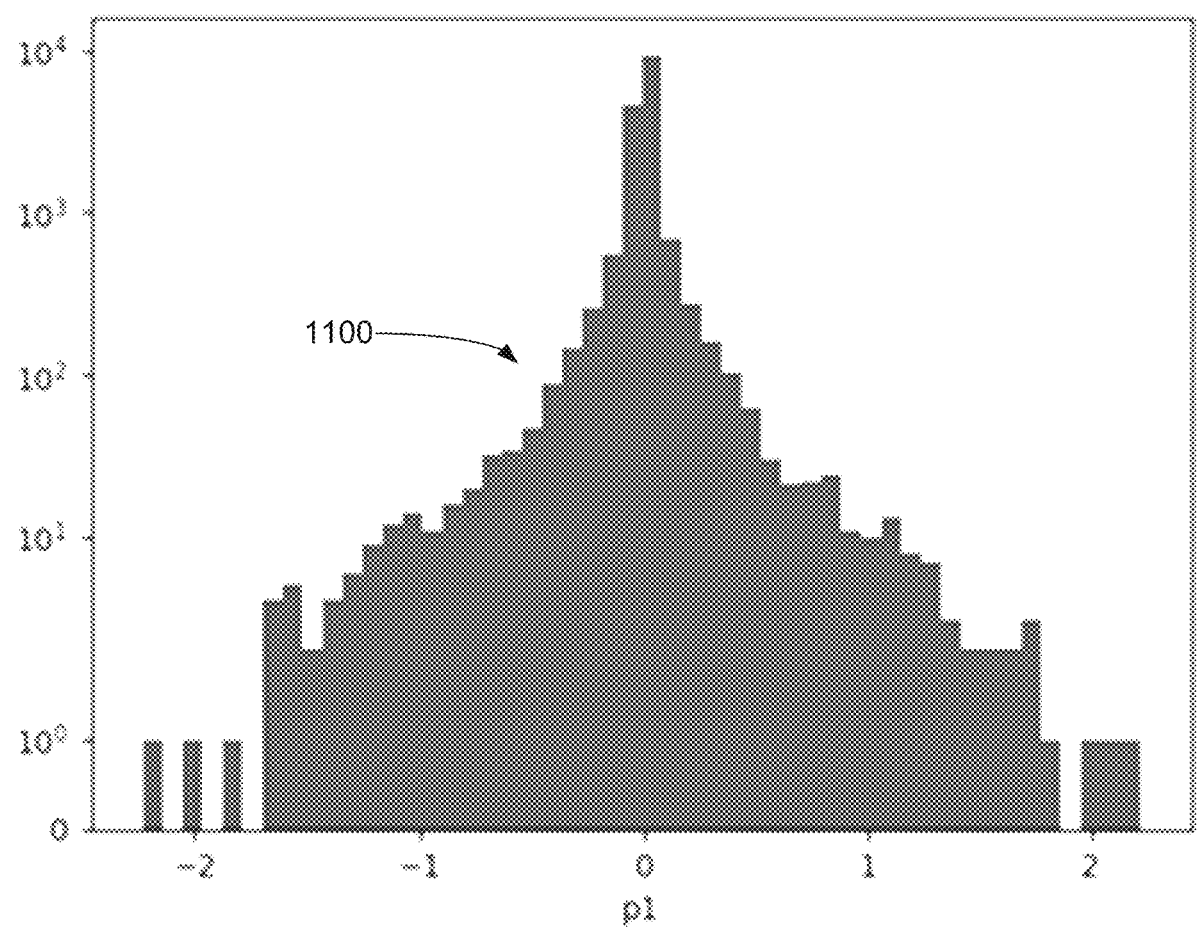
FIG. 11 depicts a distribution of values of a coefficient that is used to calibrate a threshold, in accordance with an example of the present disclosure.

In at least one example, the threshold value to which coefficients are compared was determined by analyzing a 10-minute collection of ECG samples taken from over 550 patients. Each ECG sample of the collection was transformed 406 and fit 408 to a third-degree polynomial to identify the coefficient of its first-degree monomial. Analysis of this data showed that the higher order coefficients of the polynomials are highly correlated with the first-degree coefficients. As such, the first-degree coefficients can be used to efficiently characterize any baseline drift reflected in the overall polynomials. To arrive at a threshold value appropriate for comparison purposes, first-degree coefficient values of the collection were arranged into a distribution 1100 as shown in FIG. 11 and statistically analyzed.

Figure 12:
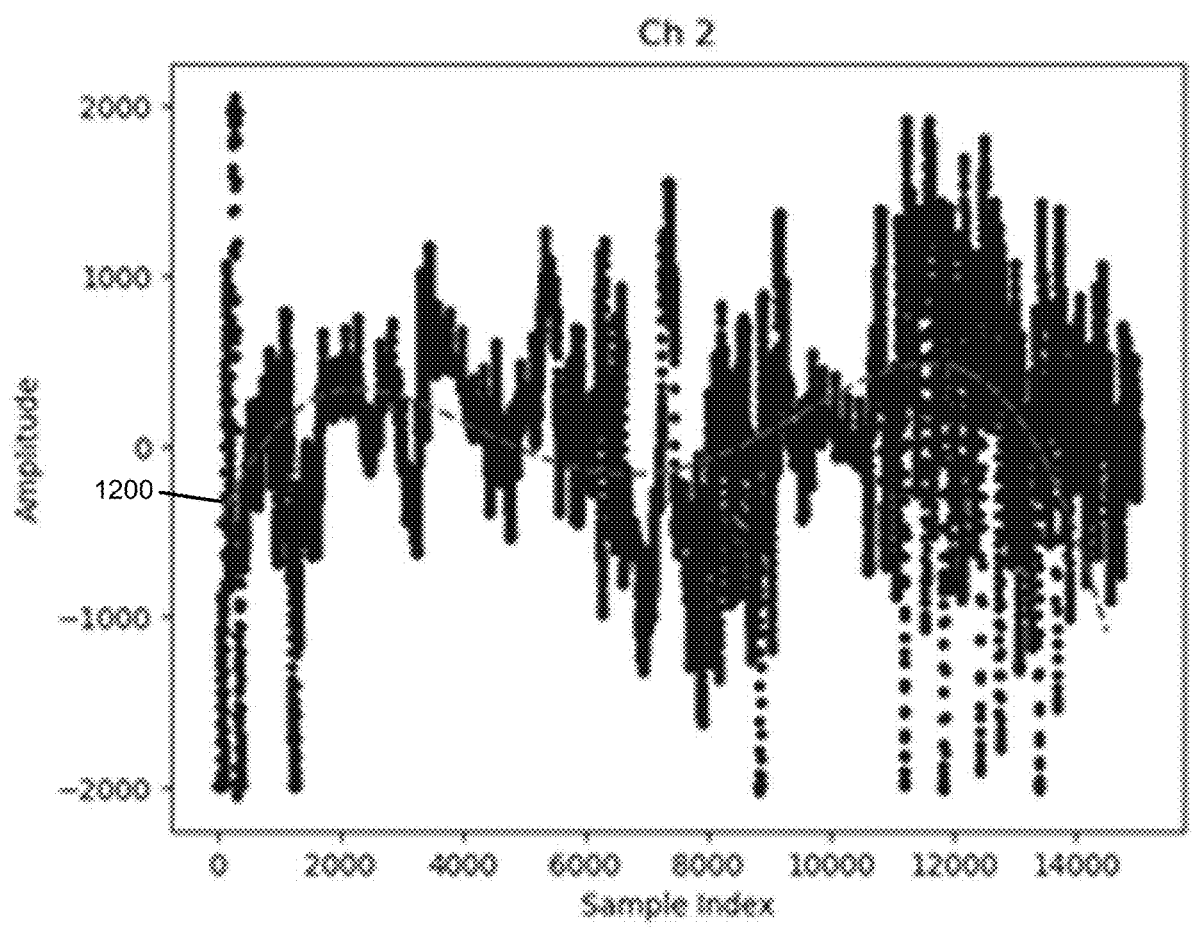
FIG. 12 depicts another example polynomial fit to an ECG sample, in accordance with an example of the present disclosure.

Continuing with the process 400, if the processor determines 410 that the coefficient value transgresses the threshold range, the processor can record 412 the selected ECG data segment as noisy. FIG. 12 illustrates a graph of an ECG data segment contaminated with a large baseline drift, as shown by the curve 1200. The x and y axes represent ECG data in a similar manner as FIGS. 9 and 10. If the processor does not determine 410 that the coefficient transgresses the threshold, or after the selected ECG data segment has been recorded 412 as noisy, the processor can determine 414 if that is the end of the ECG data segments stored in memory. If the processor determines 414 that there are additional ECG data segments, the processor can select 404 the next data segment and the process as shown in FIG. 4A can be repeated. If the processor does determine 414 that there are no additional ECG data segments, the processor can output 416 information regarding cardiac events or other similar data. For example, the processor can produce a second collection of ECG data segments that exclude any ECG data segments that are recorded as noisy. The range of acceptable threshold values can be varied or otherwise altered, e.g., via a user modifiable parameter displayed on a user interface. As such, a technician or other authorized person can adjust the thresholds as appropriate to identify the noisy ECG data segments. The second collection of ECG data segments can be regarded as groomed ECG data segments for use in one or more downstream ECG applications. The second collection of ECG data segments can be provided to, for example, a cardiac condition predictor for further analysis.

In certain implementations of process 400, the processor can be configured to perform one or more specific recording steps to record 412 the ECG data segments as noisy. For example, the processor can be configured to update metadata associated with the ECG data segments to provide an indication that the data segments are noisy. When outputting 416 the information, the processor can be configured to ignore or exclude all ECG data segments that include a noisy indication in their metadata.

In another example, the processor can be configured to update a matrix or other similar data structure stored in the memory to provide a flag or other similar indication that an ECG data segment is noisy. When outputting 416 the information, the processor can be configured to examine the matrix and remove all ECG data segments flagged as noisy, thereby excluding all noisy ECG data segments from a second collection of ECG data segments. In a similar example, the processor can be configured to store ECG data segments that are classified as not noisy in a first matrix and ECG data segments that are classified as noisy in a second matrix. When outputting 416 the information, the processor can produce a collection of ECG data segments based upon the first matrix, thereby excluding the noisy ECG data segments.

It should be appreciated that the ECG data segments as collected by, for example, system 100 as shown in FIG. 1 and described above, can occur over an extended period of time such as a period of days, weeks, months, or even years. In certain implementations, the ECG data segments that are collected and stored can be continually updated to include newly collected patient information and the process 400 as shown in FIG. 4A can be repeated periodically to update the second collection of ECG data segments. In certain implementations, the process 400 as shown in FIG. 4A can be repeated every 30 minutes, every hour, every 4 hours, every 24 hours, every week, every 2 weeks, once a month, once every 2 months, and according to various other schedules. By providing for a periodic repeating of the process 400 as shown in FIG. 4A, ECG data that has been captured since the previous processing can be analyzed and identified as noisy. Thus, the second collection of ECG data segments (i.e., the data segments that are not identified as noisy) can be updated to include additional information. As such, analysis performed by, for example, a cardiac condition predictor to determine one or more trends in the ECG data over time, can be done using an updated and continually changing ECG data set.

In certain implementations, a dual channel mode can provide additional quality checking and redundant processing to identify noise and motion artifacts in the ECG data to supplement the techniques as described herein. For example, in a dual-channel mode the ECG analyzer can perform signal quality assessment at two levels. At the first (global) level the main noise algorithm can determine if the input ECG recording is suitable for further analysis such as risk analysis (e.g., by applying a risk classifier). This first level can be done by using, for example, a QRS detection algorithm as described below in more detail. For example, two independent QRS detection modules can be applied to two ECG input channels and two detection results (e.g., a time series of timestamps indication QRS complex positions) can be obtained. For example, the two QRS detection modules can be identical or similar to each other. A matching algorithm can attempt to match a QRS complex from one channel to it correspondent in the other channel. In certain implementations, a match can be considered to occur if corresponding timestamps occur within a certain window of time. For example, the window of time may have a predetermined duration. For example, a match can be considered to occur if corresponding time stamps are within a predetermined duration of about 0.25 seconds of one another. In other examples, the predetermined window of time can be selected to be from about 0.025 seconds to about 1 second. In implementations, the window may dynamically adjust over time depending on the nature, type, and amount of underlying ECG data. For instance, if a match is not found based on a 0.25 second window, the window may automatically adjust by a predetermined step period of, for example 0.05 seconds, to be a 0.3 second window. The predetermined step periods can be set to be in a range from around 0.001 seconds to around 0.5 seconds (around 1 millisecond to around 500 milliseconds). Other values and/or ranges within the scope of the examples described herein may be used. In implementations, the processor may implement successive predetermined step periods until a predetermined maximum adjusted window period. The predetermined window, the predetermined step period, and/or the predetermined maximum adjusted window period may be specified by a user-modifiable parameter that can be adjusted by a technician or other authorized person. Initially, these values may be populated by default values in the ranges described above.

During the QRS detection algorithm, certain factors or conditions can result in an ECG signal being recorded as not suitable for further processing. For example, if there is an identified mismatch between two corresponding QRS complexes, the ECG analyzer can determine that the ECG signal is not suitable for further processing. In certain implementations, the ECG analyzer can be further configured to determine an RR interval average for each of the ECG input channels. If the RR interval average of one channel is larger or small than the other channel by a certain percentage, the ECG analyzer can record the ECG signal as noisy and not suitable for further processing. For example, if the RR intervals of the two channels differ by a predetermined variance such as 30% or more, the analyzer can determine the ECG signal to be noisy. In examples, the percentage variance for RR intervals can be predetermined to be about 10%, 15%, 20%, 25%, 35%, 40%, 45%, and 50%. While the variances herein are expressed here in percentages, in implementations, the variances can be expressed in other forms of measurement (e.g., in milliseconds, or other type of normalized units).

In certain implementations, if either condition described above occurs ((1) two or more consecutive missed corresponding timestamps, and (2) differences between the average RR intervals in excess of the predetermined variance) the ECG analyzer can determine the ECG signal is noisy and not suitable for further processing. However, it should be noted that the two conditions are shown by way of example only and, in some examples, a single condition can be used for determining whether an ECG signal is suitable for additional processing. For example, a dual channel ECG analyzer can be configured to solely analyze and compare corresponding QRS complex timestamps. Conversely, another ECG analyzer can be configured to solely analyze and compare average RR intervals.

The results of the QRS detection algorithm can be used to produce QRS complex timing information. For example, the analyzing two independent ECG signal channels as described above can produce a result that includes a series of timestamps indicating the position of the QRS complexes in the signal. In some examples, a QRS detection module (implemented by, for example, the ECG analyzer) can be configured to run a primary algorithm and a secondary algorithm. In some examples, the primary algorithm can be a real-time derivative-based algorithm similar to the Pan-Tompkins QRS detection algorithm. The primary algorithm can be configured to determine the timestamps of the QRS complexes. In some examples, the secondary algorithm can be based on a wavelet transform algorithm. The second algorithm can be configured to determine a QRS width of the detected QRS complex. The second algorithm can be further configured to detect the presence of tall T-waves in the ECG signal to reduce false detections of the primary algorithm, thereby increasing the accuracy of the overall QRS detection module.

Figure 5:
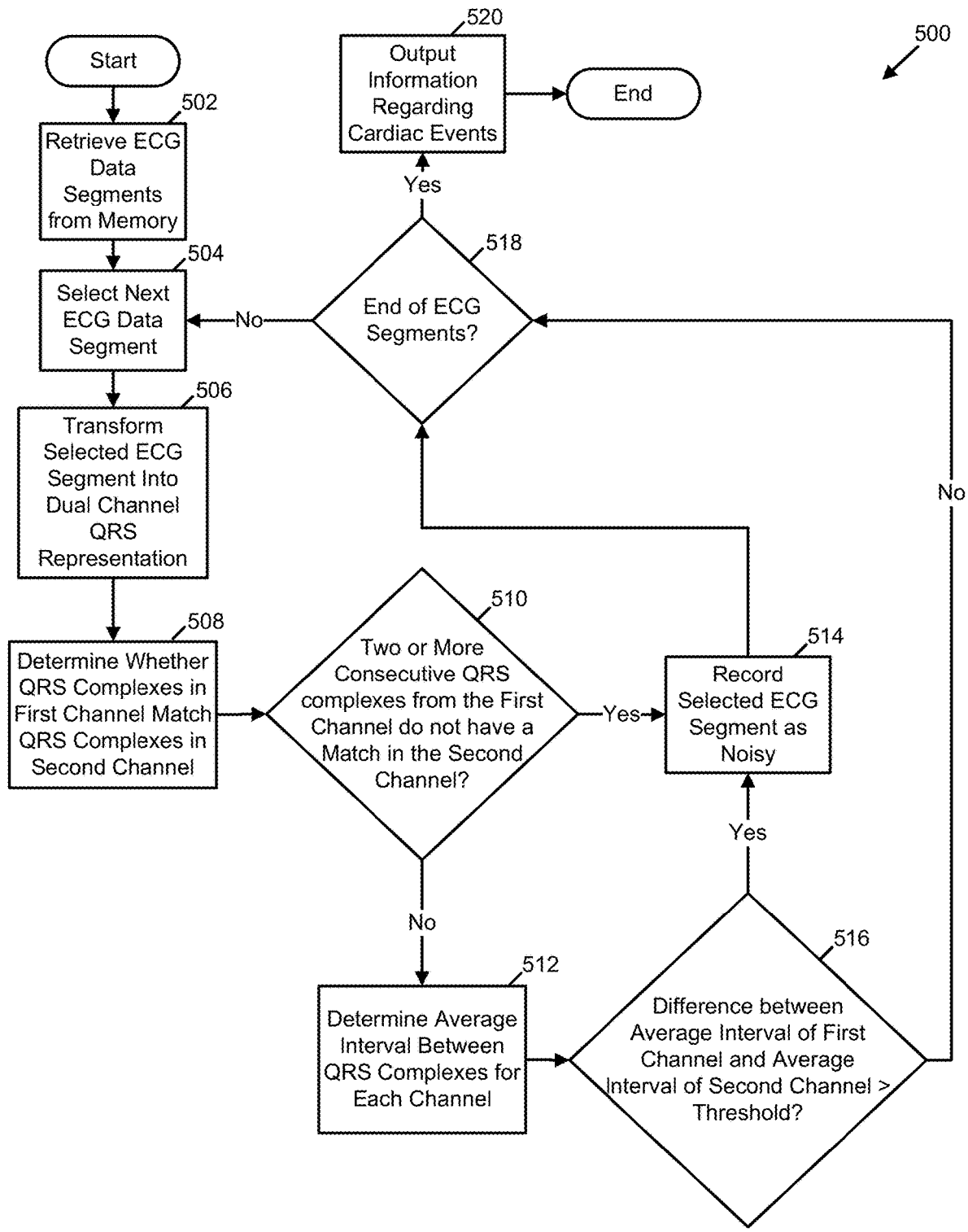
FIG. 5 depicts a sample flow for a dual channel noise discrimination process, in accordance with an example of the present disclosure.

FIG. 5 illustrates a sample process 500 for analyzing the ECG data in a dual channel mode using, for example, a processor such as processor 133 as described above configured to implement an ECG analyzer such as ECG analyzer 134 as described above. The processor can implement process 500 by retrieving 502 the ECG data segments from memory. The processor can select 504 a next ECG data segment from the retrieved data segments. If the process has just initialized, the processor can be configured to select 504 the first ECG data segment retrieved from memory. The processor can transform 506 the selected ECG data segment into a dual channel QRS representation. For example, transforming 506 the selected ECG data segment into a dual channel QRS representation can include copying the ECG data segment into two independent ECG signal channels. In some examples, the two ECG channels are for the same length of time and are synchronized but include different ECG data. The process can further identify each QRS complex within each of the two ECG signal channels and determine QRS complex timestamp information for both ECG signal channels. For example, the timestamp information can correspond to R peak occurrence within the QRS complexes. The processor can determine 508 whether the QRS complex timestamps for the first ECG signal channel match the QRS complex timestamps for the second ECG signal channel. For example, the processes can compare each QRS occurrence in the first ECG signal channel against each QRS occurrence in the second ECG signal channel to determine a time difference between QRS timestamps. If the difference between the two signal channels is within a predetermined window, the processor can determine that the two ECG signal channels having matching or corresponding QRS complexes. In certain examples, the predetermined window can be about 250 milliseconds. In other examples, the time range can be from about 25 milliseconds (0.025 seconds) to about 1000 milliseconds. Further, as previously noted, in implementations, the window may dynamically adjust over time depending on the nature, type, and amount of underlying ECG data.

As further shown in FIG. 5, the processor can determine 510 is there are two or more QRS complexes in the first ECG signal channel that do not have a corresponding match in the second ECG signal channel. If the processor determines 510 that there are two or more missed matches, the processor can record 514 the ECG data segment as noisy. Conversely, if the processor determines 510 there are not two or more missed matches, the processor can determine 512 an average RR interval for each QRS complex for each of the ECG channel signals (e.g., determine an average RR interval for each ECG signal channel). The processor can determine 516 whether a difference between the average RR interval for the first ECG signal channel differs from the average RR interval for the second ECG channel exceeds a particular threshold. If the processor does determine 516 that the difference between the RR interval for the first ECG signal channel and the RR interval for the second ECG signal channel exceeds the threshold, the processor can record 514 the ECG data segment as noisy.

For example, as noted above, the threshold can be set to 30% (or an equivalent value in milliseconds or other type of normalized value). In such an example, if the average RR interval for the first ECG signal channel varies from the RR interval for the second ECG signal channel by more than 30%, the processor can record the ECG data segment as noisy.

Referring again to process 500 as shown in FIG. 5, if the processor determines 516 that the difference between the RR interval of the first ECG signal channel and the RR interval of the second ECG signal channel is less than the threshold, or the processor has recorded 514 the ECG data segment as noisy (either by determining 510 that two or more QRS complexes do not have a matching QRS complex or by determining a difference between the RR intervals exceeds a threshold), the processor can determine 518 if there are additional ECG data segments stored in memory. If the processor determines 518 that there are additional ECG data segments, the processor can select 504 the next data segment and the process as shown in FIG. 5 can be repeated. If the processor does determine 518 that there are no additional ECG data segments, the processor can output 520 information regarding cardiac events or other similar data. For example, the processor can produce a second collection of ECG data segments that exclude any ECG data segments that are recorded as noisy. The range of acceptable threshold values as discussed above can be varied or otherwise altered, e.g., via a user modifiable parameter displayed on a user interface. As such, a technician or other authorized person can adjust the thresholds as appropriate to identify the noisy ECG data segments. The second collection of ECG data segments can be regarded as groomed ECG data segments for use in one or more downstream ECG applications. The second collection of ECG data segments can be provided to, for example, a cardiac condition predictor for further analysis.

In certain implementations of process 500, the processor can be configured to perform one or more specific recording steps to record 514 the ECG data segments as noisy. For example, the processor can be configured to update metadata associated with the ECG data segments to provide an indication that the data segments are noisy. When outputting 520 the information, the processor can be configured to ignore or exclude all ECG data segments that include a noisy indication in their metadata. In another example, the processor can be configured to update a matrix or other similar data structure stored in the memory to provide a flag or other similar indication that an ECG data segment is noisy. When outputting 520 the information, the processor can be configured to examine the matrix and remove all ECG data segments flagged as noisy, thereby excluding all noisy ECG data segments from a second collection of ECG data segments. In a similar example, the processor can be configured to store ECG data segments that are classified as not noisy in a first matrix and ECG data segments that are classified as noisy in a second matrix. When outputting 520 the information, the processor can produce a collection of ECG data segments based upon the first matrix, thereby excluding the noisy ECG data segments.

It should be noted that the determinations as made in FIG. 5 are provided by way of example only. In some examples, the processor can be configured to perform additional steps to determine if the QRS data segments are noisy. For example, the processor can be configured to determine an amplitude of each R wave in the QRS complexes and compare the amplitude to an amplitude threshold value. In certain implementations, the amplitude threshold value can be determined based upon the type of ECG device that was used to collect the ECG data segments. For example, depending upon the sensitivity of the ECG device, the amplitude threshold value can be set to a value above 10 mV. In some examples, the amplitude threshold value can be selected from a range of about 11 mV to about 20 mV. If the amplitude transgresses the amplitude threshold value, the processor can record the ECG data segment as noisy. In some examples, the processor can determine a high frequency signal-to-noise ratio (SNR) for the QRS complexes. The determined SNR can be normalized to a value between 0.0 and 1.0 (or equivalent other type of normalized scale, such as, a percentage range). The processor can compare the high frequency SNR to a SNR threshold value. In certain implementations, the SNR threshold value can be set to a value above 0.50 (or above 50%). For example, the SNR threshold value can be set (e.g., by a technician or other authorized person via a user-modifiable parameter) to approximately 0.60. In some examples, the SNR threshold value can be set to 0.55, 0.65, 0.70, 0.75, 0.80, 0.85, 0.90, 0.95, 0.99, and any threshold value therebetween. If the high frequency SNR is below the SNR signal threshold value, the processor can record the ECG data segment as noisy.

In some examples, the processor can be configured to determine isoelectric level estimates of the QRS complexes. For example, the processor can determine two different isoelectric level estimates of the QRS complex in a real-time fashion. In example phase 1, a secondary wavelet-based QRS detection algorithm can be used to determine a largest deflection after a current R wave position in time identified by the primary QRS detector. In example phase 2, a secondary QRS detection algorithm can determine a fixed number of smaller deflections (e.g., local minima/maxima points in the wavelet domain) located in a position before a current R wave as detected by the primary QRS detector. An approximate isoelectric level can be estimated based upon the average of two ECG amplitude values measured at a point in phase 1 (after the current R wave) and at a point in phase 2 (before the R wave). This process can be repeated for a subsequent R wave to obtain a second isoelectric level estimate. The processor can determine a difference between the isoelectric level estimate for a first QRS complex and a second isoelectric level estimate for an adjacent QRS complex. The processor can further compare the first isoelectric level to at least one isoelectric threshold as well as compare the difference of second isoelectric level estimates to an isoelectric difference threshold. Based upon the comparisons, the processor can identify if a particular ECG data segment is noisy.

This comparison is useful in a wearable cardiac monitoring and/or treatment device where different kinds of noise are present, including noise caused by electrode movements. An electrode movement can produce a momentary shift of the amplitude of an entire portion of the ECG signal. This shift often produces a distortion of the ECG signal. When a shift of a portion of the ECG signal occurs because of the noise, the developed isoelectric level metric can capture the magnitude of this shift.

As noted above, ECG data segments as collected by, for example, system 100 as shown in FIG. 1 and described above, can occur over an extended period of time such as a period of days, weeks, months, or even years. In certain implementations, the ECG data segments that are collected and stored can be continually updated to include newly collected patient information and the process 500 as shown in FIG. 5 can be repeated periodically to update the second collection of ECG data segments. In certain implementations, the process 500 as shown in FIG. 5 can be repeated every 30 minutes, every hour, every 4 hours, every 24 hours, every week, every 2 weeks, once a month, once every 2 months, and according to various other schedules. By providing for a periodic repeating of the process 500 as shown in FIG. 5, ECG data that has been captured since the previous processing can be analyzed and identified as noisy. Thus, the second collection of ECG data segments (i.e., the data segments that are not identified as noisy) can be updated to include additional information. As such, analysis performed by, for example, a cardiac condition predictor to determine one or more trends in the ECG data over time, can be done using an updated and continually changing ECG data set.

Figure 6A:
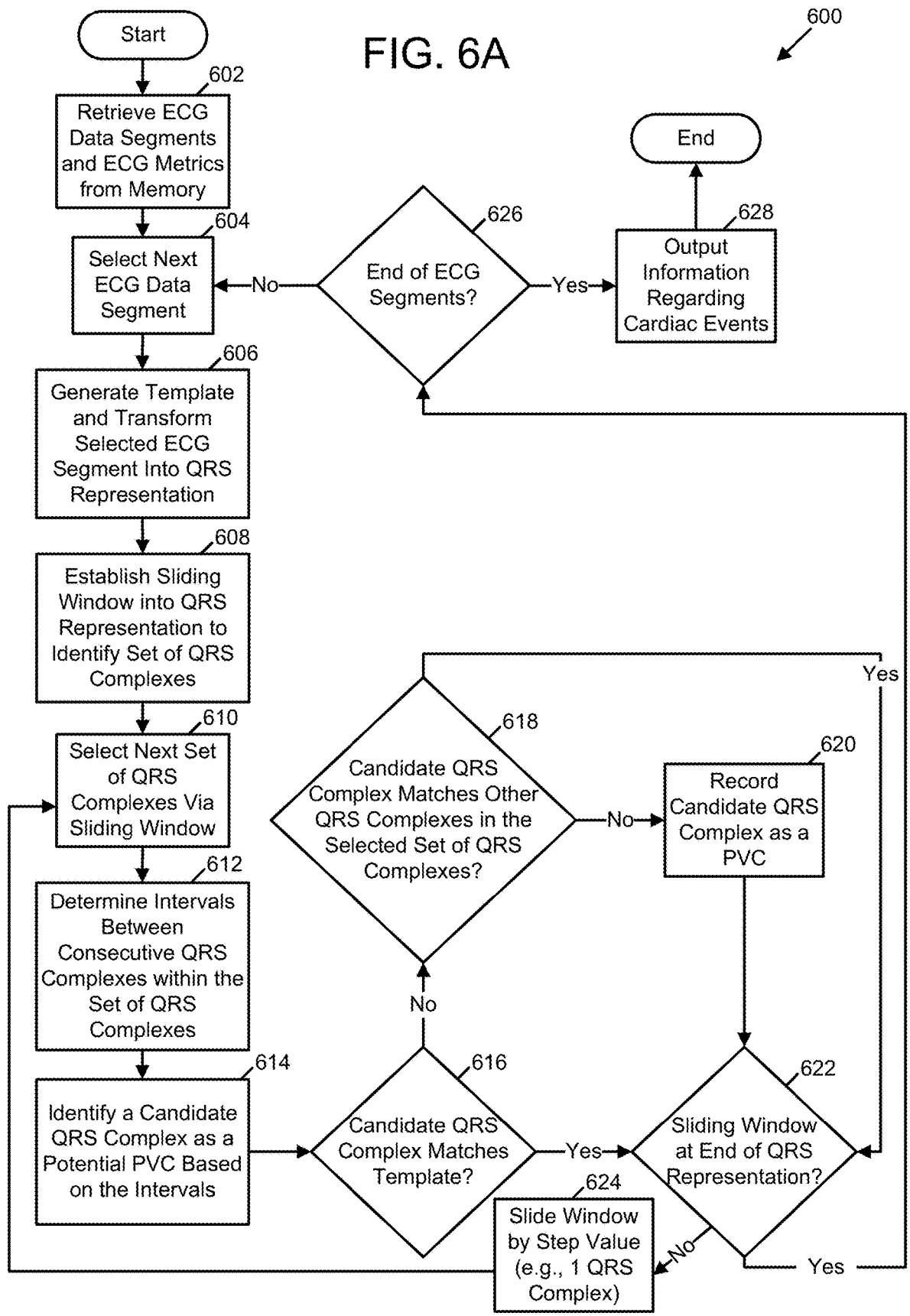
FIG. 6A depicts a sample flow for a premature ventricular contraction (PVC) discrimination process, in accordance with an example of the present disclosure.

In some implementations, an ECG analyzer can be configured to process received ECG data to determine if the ECG data is indicative of a PVC. FIG. 6A illustrates a sample PVC process 600 of analyzing ECG data for indications of a PVC in accordance with these implementations. In examples where the ECG analyzer executes the dual channel process 500, the ECG analyzer can further execute the PVC process 600 on each channel of the two channels processed by the dual channel process 500. In examples where the ECG analyzer executes the single channel process 400, the ECG analyzer can further execute the PVC process 600 on the single channel processed by the dual channel process 400.

As shown in FIG. 6A, a processing device such as processor 133 as described above or, in certain implementations, the ECG analyzer 134, can retrieve 602 ECG data segments and metadata descriptive thereof from memory. For example, the processor 133 as shown in FIG. 1A can be configured to retrieve one or more ECG data segments 137 and their associated metadata from the memory 136. In some examples, the metadata retrieved 602 can be generated and stored by the single channel process 400 or the dual channel process 500 and can include timestamps of QRS complexes within the ECG data segments, amplitude information for the ECG data segments, and/or QRS width measures of the QRS complexes.

Referring again to FIG. 6A, the processor can select 604 a next ECG data segment from the retrieved data segments. If the PVC process 600 has just initialized, the processor can be configured to select 604 the first ECG data segment retrieved from memory. The processor can transform 606 the selected ECG data segment and its associated metadata into a QRS representation of the selected ECG data segment. For example, transforming 606 the selected ECG data segment and its associated metadata into a QRS representation can include defining a template for a heartbeat that is normal for the patient within the ECG data segment and storing the ECG data in association with the metadata descriptive of the ECG data.

Figure 6B:
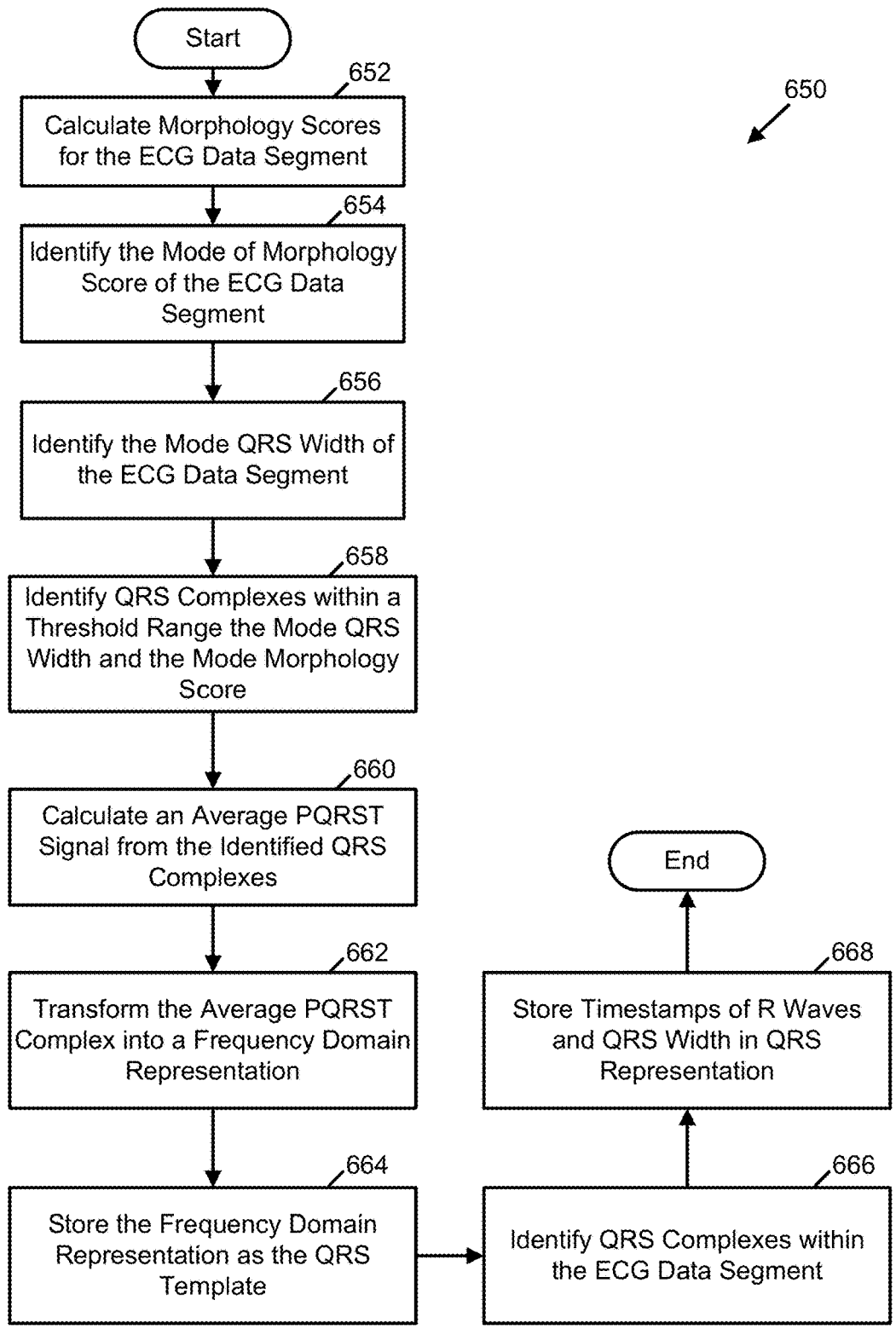
FIG. 6B depict a sample implementation of one or more process steps as shown in FIG. 6A, in accordance with an example of the present disclosure.

FIG. 6B depicts a transformation process 650 illustrative of transforming 606 the selected ECG data segment into a QRS representation in some examples. As shown in FIG. 6B, the processor can initiate the transformation process 650 by calculating 652 morphology scores for each PQRST signal including a QRS complex identified in the ECG data segment. Each morphology score can be associated with the QRS complex included in the PQRST signal. In certain examples, each morphology score is a real number auto-similarity score that is obtained by calculating the autocorrelation function of the PQRST signal. In these examples, each PQRST signal can be truncated in a fixed time window (e.g., 375 ms in duration) with respect to the detected R wave prior to calculation of the morphology score or other metric. In some examples, the morphology score can be defined as the Peak-to-Side Lobe Ratio (PSR) of the auto-correlation function of the windowed PQRST signal.

Continuing the transformation process 650, the processor can identify 654 the mode morphology score of PQRST signals within the selected ECG data segment. The processor can identify 656 the mode QRS width of QRS complexes within the selected ECG data segment. The processor can identify 658 QRS complexes associated with a morphology score within a threshold range of the mode morphology score and/or associated with a width within a threshold range of the mode QRS width. For example, the threshold range of the mode morphology score can be on a normalized scale between 0.0 and 10.0, the range normalized to exclude any extreme morphology scores. In some examples, the threshold range of the mode QRS width can be between about 45 ms and about 500 ms. For example, the threshold range of the mode QRS width can be about 100 ms. The processor can calculate 660 an average PQRST signal from PQRST signals including the identified QRS complexes. The processor can transform 662 the average PQRST signal from a time domain representation into a frequency domain representation via, for example, a Fourier transform. The frequency domain representation can comprise a vector of coefficients. The processor can store 664 the frequency domain representation as the template for the selected ECG data segment.

Next, the processor can identify 666 QRS complexes within the selected ECG data segment. For instance, the processor may access QRS complex information previously generated by the process 400 and/or 500. Alternatively or additionally, the processor can execute a QRS detector to identify 666 the QRS complexes. The processor can store 668 information descriptive of the identified QRS complexes within memory to create a QRS representation of the ECG data segment. For example, the processor may store timestamps of detected R waves present within the ECG data segment and/or store the width of the QRS complexes.

Returning to FIG. 6A, the processor can establish 608 a sliding window into the QRS representation to identify a set of QRS complexes. For instance, in some examples, the processor can establish 608 a sliding window sized to include 6 consecutive QRS complexes. In these examples, the sliding window, once established, can include (e.g., point to) the first 6 QRS complexes in the selected ECG data segment. The processor can select 610 a next set of QRS complexes via the sliding window. If the sliding window has just been established, the processor can select 610 the first QRS complexes that fall within the sliding window. If, however, the processor is executing a subsequent selection, the processor can increment the sliding window by 1 QRS complex and select 610 the next set of QRS complexes that fall within the sliding window.

Next, the processor can determine 612 RR intervals between consecutive QRS complexes within the set of QRS complexes. For example, where the set of QRS complexes include 6 members, the processor can calculate 5 RR intervals—one RR interval between each pair of consecutive QRS complexes.

The processor can identify 614 a candidate QRS complex as a potential PVC based on the RR intervals. For instance, in some examples, the processor compares adjacent RR intervals using a binary similarity function that establishes, with reference to a fixed threshold, whether the RR intervals have the same length. For example, the similarity function can include a matching function that compares the adjacent RR intervals and outputs a particular value based upon the comparison. In certain implementations, the matching function can compare the absolute value of the difference between two adjacent RR interval lengths against the sum of the two RR intervals divided by eight. Thus, the matching function can be:

if $abs(RR_0-RR_1)<((RR_0+RR_1)/8)$ output=1;

else output=0;

For instance, using the above matching function, if one RR interval $(RR_0)$ is 1 sec and the adjacent RR interval $(RR_1)$ is 0.5 sec, the similarity function outputs 0. If, however, one RR interval $(RR_0)$ is 1 sec and the adjacent RR interval $(RR_1)$ is 0.98 sec, the similarity function outputs 1. In some examples, the processor can identify a candidate QRS complex as a potential PVC where the QRS complex is a part of two consecutive RR intervals that produce similarity function output of 0 (e.g., the candidate QRS complex is at the end of a shorter RR interval and at the beginning of a longer RR interval, which is indicative of a compensatory pause).

Figure 7:
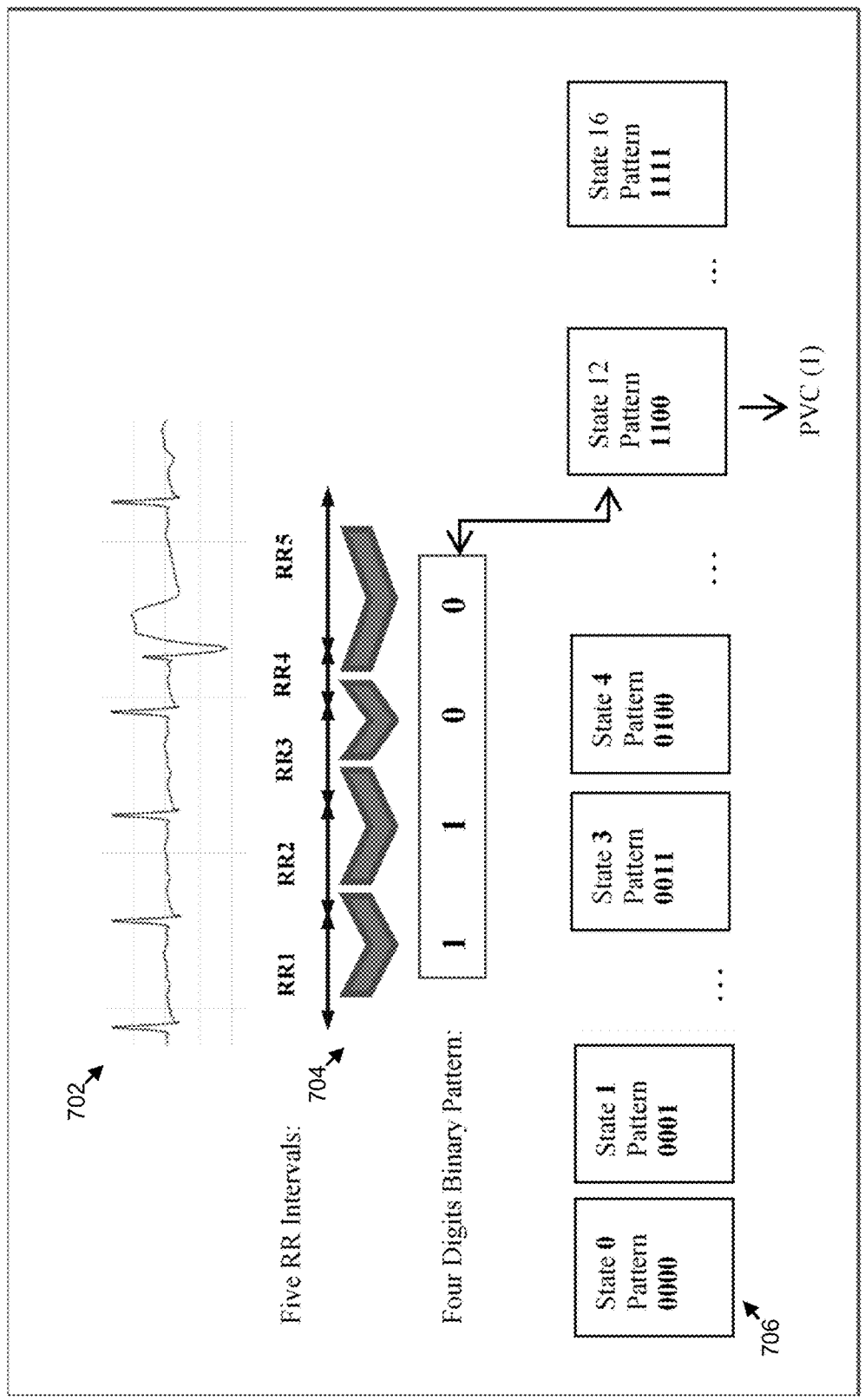
FIG. 7 depicts a process for using a state machine to classify a QRS complex, in accordance with an example of the present disclosure.

In some examples, the processor can identify 614 the candidate QRS complex by executing the similarity function for all RR intervals within the sliding window and comparing the results to a state machine that indicates all possible outcomes. Some of these outcomes are associated with, and identify, the candidate QRS complex. FIG. 7 illustrates the use of such a state machine where the sliding window includes 6 QRS complexes, in accordance with some examples.

As shown in FIG. 7, the sliding window 702 can include 6 QRS complexes and 5 RR intervals RR1-RR5. The similarity function 704 can be used to compare adjacent RR intervals, which results in, for example, a four-digit binary pattern. The state machine can include 16 binary patterns 706. Some of these binary patterns (e.g., pattern 12—"1100") can indicate the presence of a potential PVC. In the example illustrated in FIG. 7, the 5th QRS complex is identified as a candidate because it is associated with pattern 12, which indicates a compensatory pause. In other words, the R wave of $5^{th}$ QRS complex is the end point of a first RR interval and the start point of a second RR interval, which are both dissimilar from their previous, adjacent RR intervals.

Returning to FIG. 6A, the processor can determine 616 whether the candidate QRS complex matches the template. In some examples, the processor can make this determination by evaluating a similarity score that is based on the PSR of a cross-correlation function executed by the processor. The cross-correlation function can correlate the template (expressed in the time domain) with the candidate QRS complex. For example, the cross-correlation function can be:

$$C_{XY} = \sum_{k=-N}^{N} X_t Y_{t-k}$$

where X is the input signal PQRST, Y is a comparing template, and N is the number of samples that the X and Y signals are composed of, where X and Y have the same length. For example, N can be set to 131. In some examples, N can be set to any number between 10 and 1000 depending upon the sampling rate of the signal. Using the above cross-correlation function, the similarity score can be determined as:

$$\text{Similarity Score} = PSR = \frac{\max(C_{XY}) - \text{mean}(C_{xy})}{\text{std}(C_{xy})}$$

In these examples, the PQRST signal including the candidate QRS complex can be truncated into a fixed time window with respect to the detected R wave prior to execution of the cross-correlation function. If the similarity score is below a threshold value, the morphology of the candidate QRS complex deviates from the template and the candidate QRS complex may be a PVC. In this situation, the processor determines 616 that the candidate QRS complex does not match the template.

Next, the processor can determine 618 whether the candidate QRS complex matches other QRS complexes in the selected set of QRS complexes. In some examples, the processor can make this determination by evaluating similarity scores between the candidate QRS complex and a well-defined subset of QRS complexes among the selected set of QRS complexes. If these similarity scores are below the defined threshold, then the processor can determine 618 that the candidate QRS complex does not match the other QRS complexes in the selected set of QRS complexes and record 620 the candidate QRS complex as a PVC.

If the processor determines 616 that the candidate QRS complex matches the template or the processor records 620 the QRS complex as a PVC, the processor can determine 622 whether the sliding window is at the end of the QRS representation. If the processor determines 622 that the sliding window is not at the end of the QRS representation, the processor can increment 624 the sliding window by a step value (e.g., 1 QRS complex) and select 610 the next set of QRS complexes via the sliding window.

If the processor determines 622 that the sliding window is at the end of the QRS representation, the processor can determine 626 whether processing is at the end of the ECG data segments. If the processor determines 626 that processing is not at the end of the ECG data segments, the processor can select 604 the next ECG data segment. If the processor determines 626 that processing is at the end of the ECG data segment, the processor can output 628 information regarding cardiac events. For example, the processor can output a 0 or a 1 to indicate whether a PVC was detected and, where a PVC was detected, can output an integer identifying which QRS complex was recorded as a PVC.

Figure 8:
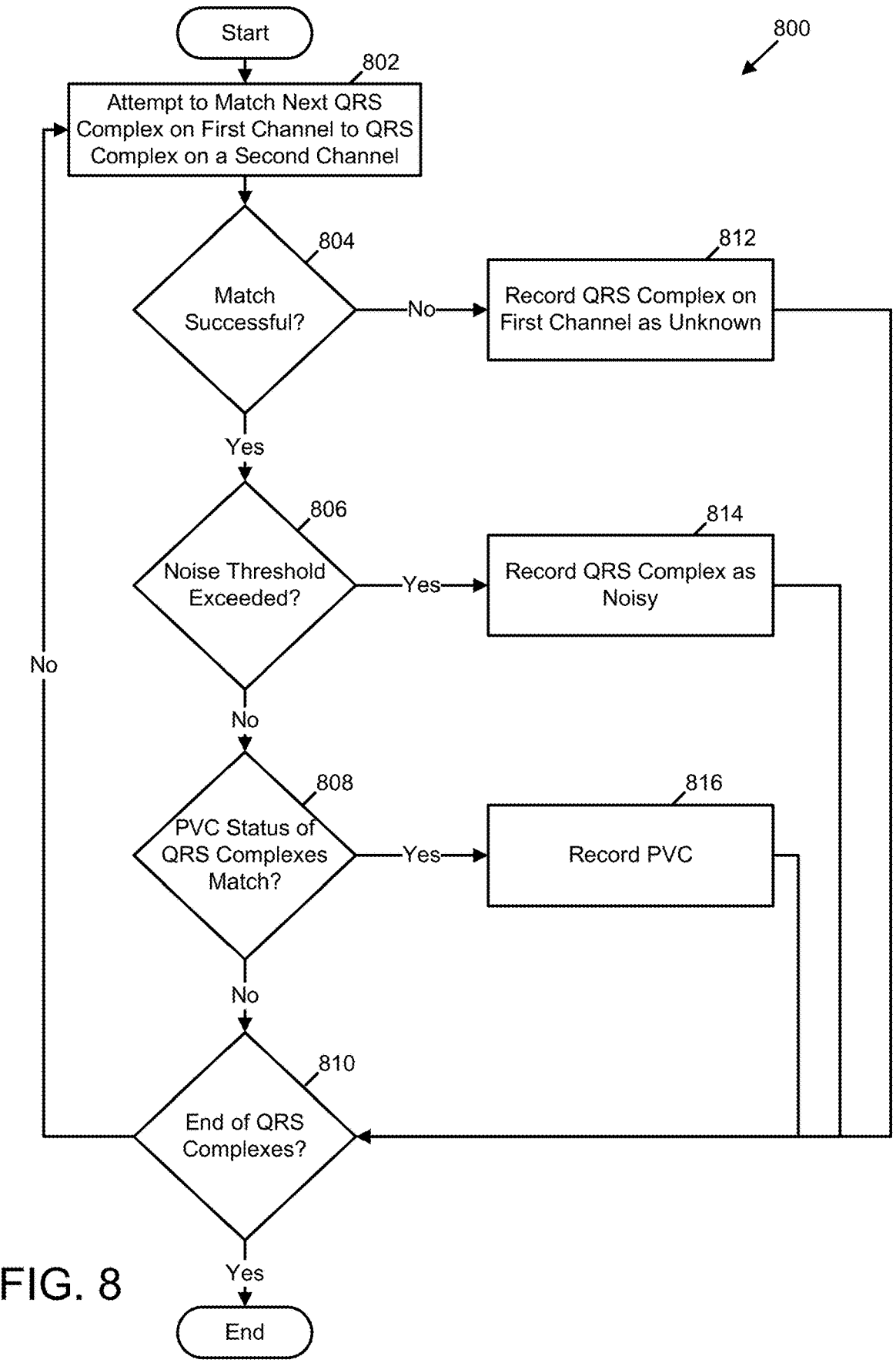
FIG. 8 depicts a process for a dual channel PVC discrimination process, in accordance with an example of the present disclosure.

In some implementations, an ECG analyzer can be configured to process the output of the PVC process 600 for each of two channels to determine a unique count of PVC beats. FIG. 8 illustrates a sample dual PVC process 800 in accordance with these implementations. In examples where the ECG analyzer executes the PVC process 600 on each channel of the two channels processed by the dual channel process 500, the ECG analyzer can further execute the dual PVC process 800 as described below.

As shown in FIG. 8, the dual PVC process 800 starts with the processor attempting to match 802 the next QRS complex identified on a first channel to a QRS complex identified on a second channel. If the dual PVC process 800 has just initialized, the processor can be configured to attempt to match 802 the first QRS complex on the first channel to a QRS complex on the second channel. Otherwise, the processor can increment to the next QRS complex on the first channel prior to attempting to match 802 it to a QRS complex on the second channel. In some examples, the processor can attempt to match 802 QRS complexes on the first and second channels by comparing temporal locations or positions of the first and second QRS complexes within the ECG data segment. If the positions of the first and second QRS complexes fit within an overall time window, a successful match is recorded. Otherwise, an unsuccessful match is recorded.

Next, the processor can determine 804 whether a successful match was recorded. If the processor determines 804 that an unsuccessful match was recorded, the processor can record 812 the QRS complex on the first channel as unknown and proceed to determine 810 whether processing has reached the end of QRS complexes are present on the first channel. If the processor determines 810 that processing has reached the end of the QRS complexes on the first channel, the dual PVC process 800 ends. If the processor determines 810 that processing has not reached the end of the QRS complexes on the first channel, the processor can return to attempting to match 802 the next QRS complex on the first channel to a QRS complex on the second channel.

If the processor determines 804 that a successful match was recorded, the processor can determine 806 whether a noise threshold was exceeded. For instance, the processor can execute a function that takes input noise metrics associated with each QRS complex and determines whether the input noise metrics exceed a well-defined set of thresholds. If the processor determines 806 that the noise metrics exceed a threshold, the processor can record 814 the QRS complex as noisy and proceeds to determine 810 whether processing as reached the end of the QRS complexes present on the first channel.

If the processor determines 806 that the noise threshold was not exceeded, the processor can determine 808 whether the matched QRS complexes on the first and second channel were both recorded as PVCs. For instance, the processor can execute a function that takes as input two integers (e.g., a number between 1 and 16, where a state machine such as the state machine described above is implemented) that each identify whether a QRS complex recorded as a PVC. This function can output an integer indicating whether the beat is normal or a PVC.

If the processor determines 808 that the matched QRS complexes were both recorded as PVCs, the processor can confirm 816 this recordation by, for example, incrementing a unique PVC count associated with the ECG data segment. If the processor determines 808 that either or both of the of the matched QRS complexes were not recorded as PVCs, the processor can determine 810 whether processing has reached the end of the QRS complexes on the first channel.

PVC counting processes such as those described above provide an accounting of PVC within an ECG data segment. For example, the PVC count metric or metrics can be subsequently used to a variety of useful ends, including to help estimate or predict a patient's future cardiac state.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any example can be combined with one or more features of any other example.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An electrocardiogram (ECG) processing system for processing noisy ECG data segments, comprising:

one or more network interfaces configured to receive a first collection of ECG data segments from wearable medical devices associated with a plurality of patients, each wearable medical device of the wearable medical devices being configured to be continuously worn by a patient for an extended period of time;

a memory configured to store the first collection of ECG data segments; and one or more processors and associated circuitry coupled with the memory, the one or more processors being configured to
- (a) retrieve the first collection of ECG data segments from the memory,
- (b) for each ECG data segment of the first collection of ECG data segments,
  - (i) transform the ECG data segment into a corresponding baseline representation of the ECG data segment by dividing the ECG data segment into a plurality of sample periods, each sample period of the plurality of sample periods spanning between 2 and 8 seconds, and
    for each sample period within the plurality of sample periods, removing ECG data collected within the sample period that transgresses one or more threshold values to generate the baseline representation of the ECG data segment,
  - (ii) fit the baseline representation of the ECG data segment to a function comprising at least one first-degree coefficient,
  - (iii) compare the at least one first-degree coefficient of the function to a baseline drift threshold, the at least one first-degree coefficient characterizing baseline drift in the baseline representation of the ECG data segment, and
  - (iv) identify the ECG data segment as a noisy ECG data segment where the at least one first-degree coefficient of the function transgresses the baseline drift threshold,
- (c) produce a second collection of ECG data segments from the first collection of ECG data segments that excludes the noisy ECG data segments, and
- (d) output one or more ECG metrics relating to the plurality of patients based on the second collection of ECG data segments.

2. The ECG processing system of claim 1, wherein the first collection of ECG data segments is updated over time to include additional ECG data segments.

3. The ECG processing system of claim 2, wherein the one or more processors is configured to periodically repeat steps (a)-(d) after a duration of time.

4. The ECG processing system of claim 3, wherein duration of time comprises at least one of 30 minutes, 1 hour, 4 hours, 24 hours, 1 week, 2 weeks, and 1 month.

5. The ECG processing system of claim 3, wherein the one or more processors is configured to determine one or more trends in the one or more ECG metrics over the duration of time.

6. The ECG processing system of claim 1, wherein the function comprises a polynomial.

7. The ECG processing system of claim 6, wherein the at least one first-degree coefficient comprises a coefficient of a first-degree monomial of a third-degree polynomial.

8. The ECG processing system of claim 1, wherein the baseline drift threshold comprises a range of threshold values between −0.5 and 0.5.

9. The ECG processing system of claim 1, wherein the one or more processors are configured to use linear regression to fit the baseline representation of the ECG data segment to the function.

10. The ECG processing system of claim 1, wherein each of the ECG data segments spans between 15 and 120 seconds.

11. The ECG processing system of claim 1, wherein each of the ECG data segments comprises an average length of at least one of about 15 seconds, about 30 seconds, about 45 seconds, about 60 seconds, about 90 seconds, about 120 seconds, about 150 seconds, about 180 seconds, about 5 minutes, about 10 minutes, and about 15 minutes.

12. The ECG processing system of claim 1, wherein the one or more ECG metrics comprises a heart rate metric, a heart rate variability metric, a QRS duration metric, a QT interval metric, a heart rate turbulence metric, and/or pre-ventricular contraction (PVC) burden metric.

13. The ECG processing system of claim 1, wherein the one or more processors are configured to provide the one or more ECG metrics to a cardiac prediction process.

14. The ECG processing system of claim 1, wherein the one or more ECG metrics can be used by the one or more processors to determine or one or more arrhythmia events comprising ventricular tachycardia, ventricular fibrillation, bradycardia, tachycardia, asystole, pause, bigeminy, and/or trigeminy.

15. The ECG processing system of claim 1, further comprising the wearable medical devices, wherein the wearable medical devices comprise dry ECG electrodes configured to acquire ECG signals.

16. The ECG processing system of claim 1, further comprising the wearable medical devices, wherein the wearable medical devices comprise adhesively attached ECG electrodes configured to acquire ECG signals.

17. The ECG processing system of claim 1, wherein the one or more ECG metrics are analyzed by the one or more processors to determine a current heart failure condition of at least one of the plurality of patients.

18. The ECG processing system of claim 17, wherein the one or more ECG metrics are analyzed by the one or more processors to determine a change in the current heart failure condition of the at least one of the plurality of patients.

19. The ECG processing system of claim 1, wherein the one or more processors are further configured to:
- determine, for each sample period within the plurality of sample periods, a mean of ECG data collected within the sample period;
- determine, for each sample period within the plurality of sample periods, a standard deviation of ECG data collected within the sample period; and
- determine, for each sample period within the plurality of sample periods, the baseline drift threshold based on the mean of the ECG data collected within the sample period and the standard deviation of the ECG data collected within the sample period.

20. The ECG processing system of claim 1, further comprising the wearable medical devices, wherein the wearable medical devices comprise a first wearable medical device associated with a first heart failure patient and a second wearable medical device associated with a second heart failure patient.

* * * * *